United States Patent
Kurtz et al.

(10) Patent No.: US 6,290,946 B1
(45) Date of Patent: Sep. 18, 2001

(54) ANIONIC POLYMERS AS TOXIN BINDERS AND ANTIBACTERIAL AGENTS

(75) Inventors: Caroline Isabelle Bacon Kurtz, Sudbury; Richard Fitzpatrick, Marblehead, both of MA (US)

(73) Assignee: GelTex Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 09/569,276

(22) Filed: May 11, 2000

Related U.S. Application Data

(63) Continuation-in-part of application No. 09/541,268, filed on Apr. 3, 2000.
(60) Provisional application No. 60/133,975, filed on May 13, 1999.

(51) Int. Cl.⁷ ..................................................... A61K 31/74
(52) U.S. Cl. ................. 424/78.08; 424/78.1; 424/78.01; 424/78.18
(58) Field of Search .................. 424/78.01, 78.1, 424/167.1, 78.08, 78.18

(56) References Cited

U.S. PATENT DOCUMENTS

| | | | |
|---|---|---|---|
| 3,224,941 | 12/1965 | Nosh et al. | 167/55 |
| 3,466,365 | 9/1969 | Schlesinger | 424/78 |

(List continued on next page.)

FOREIGN PATENT DOCUMENTS

| | | |
|---|---|---|
| 1114997 | 12/1981 | (CA) . |
| 0 800 862 A1 | 10/1997 | (EP) . |
| 93/14146 | 7/1993 | (WO) . |
| 99/20285 | 4/1999 | (WO) . |

OTHER PUBLICATIONS

Regelson, W., "The Antimitotic Activity of Polyanions," *Advances in Chemotherapy* 3:303–371 (1968).

"Functional Polymers with Biologically Active Groups," *J. Macromol. Sci.–Chem.*, A13(3), pp. 415–439 (1979).

Higaki, M., et al., "Enhancement of Immune Response to Intranasal Influenza HA Vaccine by Microparticle Resin", *Vaccine* 16(7):741–745 (1998).

De Rosa, A., et al., "Effects of Sodium Polystyrene Sulfonate on Gingival Plaque: Microbiological Investigation and Clinical Follow–Up", *Microbiologica* 19:357–362 (1996).

Carson, D.L., et al., "Ocular Toxicity of Ciprofloxacin/PSSA Fluoroquinolone Antibacterial Solution in Pigmented Rabbits", *J. Toxicol.—Cut. & Ocular Toxicol.* 15(2):165–178 (1996).

(List continued on next page.)

Primary Examiner—Thurman K. Page
Assistant Examiner—Blessing Fubara
(74) Attorney, Agent, or Firm—Hamilton, Brook, Smith & Reynolds, P.C.

(57) ABSTRACT

The present invention relates to a method of inhibiting a toxin in an animal, such as a human, by administering to the animal a therapeutically effective amount of a polymer having a plurality of pendant acid functional groups which are directly attached to the polymer backbone or attached to the polymer backbone by a spacer group. The spacer group can have a length in the range from 0 to about 20 atoms. The toxin is, typically, an exotoxin secreted by a pathogenic microorganism, such as a bacterium.

19 Claims, 1 Drawing Sheet

U.S. PATENT DOCUMENTS

| | | | |
|---|---|---|---|
| 3,987,163 | * 10/1976 | Rankin | 424/78 |
| 4,362,711 | 12/1982 | Cerami | 424/33 |
| 4,395,392 | 7/1983 | Wolgemuth | 424/78 |
| 5,071,759 | 12/1991 | Rothman et al. | 435/240 |
| 5,093,130 | 3/1992 | Fujii et al. | 424/463 |
| 5,128,323 | 7/1992 | Pranger | 514/23 |
| 5,149,523 | 9/1992 | Lundberg et al. | 424/78.1 |
| 5,149,543 | 9/1992 | Cohen et al. | 424/499 |
| 5,171,738 | 12/1992 | Kodama et al. | 424/78.17 |
| 5,231,003 | 7/1993 | Coughlin et al. | 435/7.32 |
| 5,277,820 | 1/1994 | Ash | 210/646 |
| 5,308,701 | 5/1994 | Cohen et al. | 428/402.22 |
| 5,324,718 | 6/1994 | Loftsson | 514/58 |
| 5,435,821 | 7/1995 | Duvdevani et al. | 71/28 |
| 5,474,765 | 12/1995 | Thorpe | 424/178.17 |
| 5,484,773 | 1/1996 | Heerze et al. | 514/23 |
| 5,601,823 | 2/1997 | Williams et al. | 424/167.1 |
| 5,610,023 | 3/1997 | Deutsch | 435/7.32 |
| 5,614,559 | 3/1997 | Singh et al. | 514/577 |
| 5,618,825 | 4/1997 | Baldwin et al. | 514/317 |
| 5,635,606 | 6/1997 | Heerze et al. | 530/412 |
| 5,643,562 | 7/1997 | Kisilevsky et al. | 424/78.31 |
| 5,677,343 | 10/1997 | Singh et al. | 514/577 |
| 5,679,775 | 10/1997 | Boos et al. | 530/351 |
| 5,736,139 | 4/1998 | Kink et al. | 424/164.1 |
| 5,762,934 | 6/1998 | Williams et al. | 424/157.1 |
| 5,773,000 | * 6/1998 | Bostwick et al. | 424/167.1 |
| 5,800,803 | 9/1998 | Mirajkar et al. | 424/54 |
| 6,007,803 | * 12/1999 | Mandeville, III et al. | 424/78.1 |
| 6,060,235 | 5/2000 | Neenan et al. | 435/5 |
| 6,075,050 | 6/2000 | Singh et al. | 514/517 |

OTHER PUBLICATIONS

Moreau, J.M., et al., "Effectiveness of Ciprofloxacin–Polystyrene Sulfonate (PSS), Ciprofloxacin and Ofloxacin In A *Staphylococcus Keratitis* Model" (Abstract), *Current Eye Research* 17(8):808–812 (1998).

Engel, L.S., "The Effectiveness of Two Ciprofloxacin Formulations for Experimental *Pseudomonas and Staphylococcus Keratitis*", *Jpn J. Opthalmol.*, 40(2):212–219 (1996).

Zeitlin, L., et al., "Tests of Vaginal Microbicides in the Mouse Genital Herpes Model", *Contraception*, 56:329–335 (1997).

Rashid, A., et al., "Necrosis of the Gastrointestinal Tract in Uremic Patients as a Result of Sodium Polystyrene Sulfonate (Kayexalate) in Sorbitol", *American J. of Surgical Pathology*, 21(1):60–69 (1997).

Gerstman, B., et al., "Intestinal Necrosis Associated with Postoperative Orally Administered Sodium Polystyrene Sulfonate in Sorbitol", *Am. J. of Kidney Diseases*, 20(2):159–161 (1992).

Linakis, J.G., et al., "Multiple–Dose Sodium Polystyrene Sulfonate in Lithium Intoxication: An Animal Model", *Pharmacology & Toxicology*, 70:38–40 (1992).

Mohan, P., et al., "Sulfonic Acid Polymers as a New Class of Human Immunodeficiency Virus Inhibitors", *Antiviral Research*, 18:139–150 (1992).

Taylor, N.S., et al., "Binding of Clostridium Difficile Cytotoxin and Vancomycin by Anion–Exchange Resins", *J. of Infectious Diseases*, 141(1):92–97 (1980).

Burbige, E.J., et al., "Pseudomembranous Colitis", *JAMA*, 231(11):1157–1158 (1975).

Lipman, N.S., et al., "Utilization of Cholestyramine Resin as a Preventive Treatment for Antibiotic (Clindamycin) Induced Enterotoxaemia in the Rabbit", *Laboratory Animals*, 26:1–8 (1992).

Bartlett, J.G., et al., *The Lancet*, 258–259 (1978).

Tedesco, F.J., "Treatment of Recurrent Antibiotic–Associated Pseudomembranes Colitis", *Am. J. of Gastroenterology*, 77(4):220–221 (1982).

* cited by examiner

ANIONIC POLYMERS AS TOXIN BINDERS AND ANTIBACTERIAL AGENTS

RELATED APPLICATION

This application claims priority to U.S. application Ser. No.: 09/541,268, filed Apr. 3, 2000 and the benefit of Provisional application Ser. No.: 60/133,975, filed May 13, 1999, the contents of which are incorporated herein by reference in its entirety.

BACKGROUND OF THE INVENTION

Many pathogens produce toxins which are detrimental, and in some cases, lethal, to the host organism. Toxins produced by pathogens can be classified into two general categories, exotoxins and endotoxins.

Exotoxins are generally proteins or polypeptides. These toxins, which are secreted by the pathogen, can travel within the host and cause damage in regions of the host far removed from the infection site. Symptoms associated with exotoxins vary greatly and include hemolysis, systemic shock, destruction of leukocytes, vomiting, paralysis and diarrhea.

Enterotoxins are exotoxins which act on the small intestine and cause massive secretion of fluid into the intestinal lumen, leading to diarrhea. Enterotoxins are produced by a variety of bacteria, including the food-poisoning organisms *Staphylococcus aureus, Clostridium perfringens,* and *Bacillus cereus,* and the intestinal pathogens *Vibrio cholerae, Escherichia coli,* and *Salmonella enteritidis.*

Endotoxins are lipopolysaccharides/lipoproteins found in the outer layer of the cell walls of gram-negative bacteria. These lipopolysaccharides are bound to the cell membrane and are released upon cytolysis. Symptoms associated with the release of endotoxins include fever, diarrhea and vomiting. Specifically, endotoxins stimulate host cells to release proteins, endogenous pyrogens, which affect the area of the brain which regulates body temperature. In addition to fever, diarrhea and vomiting, the host animal may experience a rapid decrease in lymphocyte, leukocyte, and platelet numbers, and enter into a general inflammatory state.

Although endotoxins are less toxic than exotoxins, large doses of endotoxins can cause death, generally through hemorrhagic shock and tissue necrosis. Examples of bacteria which produce endotoxins include bacteria of the genera Escherichia, Shigella, and especially Salmonella.

In some cases, the active disease caused by an exotoxin can be treated by administering an antitoxin to the patient. An antitoxin comprises antibodies to the toxin derived from the serum of an animal, typically a horse, which has been immunized by injection of a toxoid, a nontoxic derivative of the toxin. However, the effectiveness of antitoxins is limited because toxins are rapidly taken up by cells and become unavailable to the antibodies. Furthermore, the patient's immune system can respond to foreign proteins present in the antitoxin, creating a condition known as serum sickness.

*Clostridium difficile* has become one of the most common nosocomially-acquired organisms in hospitals and long term care institutions. The organism typically infects patients whose normal intestinal flora has been disturbed by the administration of a broad-spectrum antibiotic. The diarrhea and inflammatory colitis associated with infection represent a serious medical/surgical complication leading to increased morbidity and mortality, and prolonging hospital stays by an average of nearly three weeks. This is especially true for the elderly and for patients with serious underlying diseases who are the most likely to develop the infection. *C. difficile* associated diarrhea (CDAD) represents a major economic burden to the healthcare system, conservatively estimated at $3–6 billion per year in excess hospital costs in the U.S. alone.

Currently, treatments for CDAD are inadequate. Such treatments include discontinuing the antibiotic that caused CDAD to manifest and allow the normal colonic flora to recover as rapidly as possible. In most cases however, that is not sufficient and yet another antibiotic, metronidazole, or vancomycin, are used to kill the *C. difficile* organisms. Symptomatic improvement with metronidazole is slow, typically taking 4 to 8 days. In addition, because metronidazole also alters the normal flora by eradicating most anaerobes from the gut, 20% of treated patients have a relapse or recurrence of CDAD, usually within 1 to 2 weeks of stopping therapy. In severe or recurrent cases of CDAD, vancomycin may be used. However, this drug has a similar rate of relapse to metronidazole and also has the potential for the undesirable side effect of causing selection for multi-drug resistant enterococci and staphylococci.

Diarrhea and colitis are a direct result of intestinal damage and inflammation caused by *C. difficile* Toxins A and B. The Toxins A and B, produced by *C. difficile,* damage the intestinal mucosa and are the etiologic agents responsible for the inflammatory colitis. Currently, no therapies are available to inhibit the bacterial toxins produced by *C. difficile* and which are responsible for the intestinal damage and inflammation leading to diarrhea and colitis. Pharmaceuticals that can inhibit Toxins A and B are the most logical approach to CDAD therapy.

Therefore, a need exists for an improved method of treating a toxin-mediated condition which significantly reduces or eliminates the above-mentioned problems.

SUMMARY OF THE INVENTION

The present invention relates to a method of inhibiting a toxin in an animal, such as a human, by administering to the animal a therapeutically effective amount of a polymer having a plurality of pendant acid functional groups which are directly attached to the polymer backbone or attached to the polymer backbone by a spacer group. The spacer group can have a length in the range from 0 to about 20 atoms. The toxin is, typically, an exotoxin secreted by a pathogenic microorganism, such as a bacterium. In a preferred embodiment, the polymer is substantially free of acid anhydrides.

In another embodiment, the present invention relates to pharmaceutical compositions comprising anionic polymers and methods for treatment of CDAD and other antibiotic associated diarrhea (AAD) in mammals and particularly in humans. The therapeutic compositions of the invention preferably inactivate both *C. difficile* Toxins A and B and are highly effective in preventing the development of CDAD (prophylactic treatment) as well as to prevent recurrence and relapse of CDAD when used as a monotherapy or when used as co-therapy with antibiotics (e.g. metronidazole and vancomycin).

As discussed above, the polymers utilized in the described methods are substituted by acid or anionic groups. Suitable acid functional groups include carboxylic acid, sulfonic acid, phosphonic acid, hydrosulfate, hydrophosphate, sulfamic acid and boronic acid groups. The acid groups can also be present in the conjugate base form in combination with a suitable cation.

In one embodiment, the polymer to be administered is a copolymer characterized by a first monomer or repeat unit having a pendant acid functional group and a second monomer or repeat unit having a pendant hydrophobic group. In another embodiment, the polymer is characterized by a monomer or repeat unit having both a pendant acid functional group and a pendant hydrophobic group. The polymer to be administered can, optionally, be further characterized by a monomer or repeat unit comprising a neutral hydrophilic group, such as a hydroxyl group or an amide group.

Preferred therapeutic compositions for use in the methods of the invention comprise poly(styrenesulfonate) and salts thereof. Preferred methods of the invention include administering a therapeutically effective amount of a composition of the invention to a patient either as a cotherapy with the broad spectrum antibiotic which may otherwise precipitate the onset of CDAD or AAD, but for the presence of the polystyrene-containing composition of the invention. Cotherapy with a broad-spectrum antibiotic will not interfere with the effectiveness of the antibiotic but at the same time will prevent the onset of CDAD or AAD.

In another embodiment, the compositions of the invention may be used either alone as a monotherapy or as cotherapy with metronidazole, vancomycin or other antibiotics used to treat CDAD or AAD, after the onset of disease. In yet another embodiment, the compositions of the invention may be used either alone or as a cotherapy with other antibiotics to prevent the recurrence or relapse of disease.

The present invention has many advantages. For example, the compositions used in the methods of the invention are easily prepared using standard techniques of polymer synthesis and inexpensive starting materials. The methods of the invention generally do not interfere with the broad spectrum antibiotics often necessary to treat other infections of the body and thus can be used in conjunction with broad spectrum antibiotics. Additionally, the patient can be simultaneously protected from the adverse side effects of such broad spectrum antibiotics often leading to CDAD or AAD when the prophylactic treatment regimens of the invention are used in conjunction with delivery of broad spectrum antibiotics to the patient. Likewise, the treatment regimens of the invention generally do not interfere with the actions of metronidazole or vancomycin and can therefore, also be used in conjunction with such treatments after the onset of disease or post treatment to prevent recurrence and relapse of disease. Additionally, the compositions and methods of the invention may be used as monotherapy to prevent the onset of disease (prophylactic), to treat disease after onset, or to prevent relapse. Monotherapy in accordance with the invention is particularly advantageous when patients cannot tolerate antibiotic regimens.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
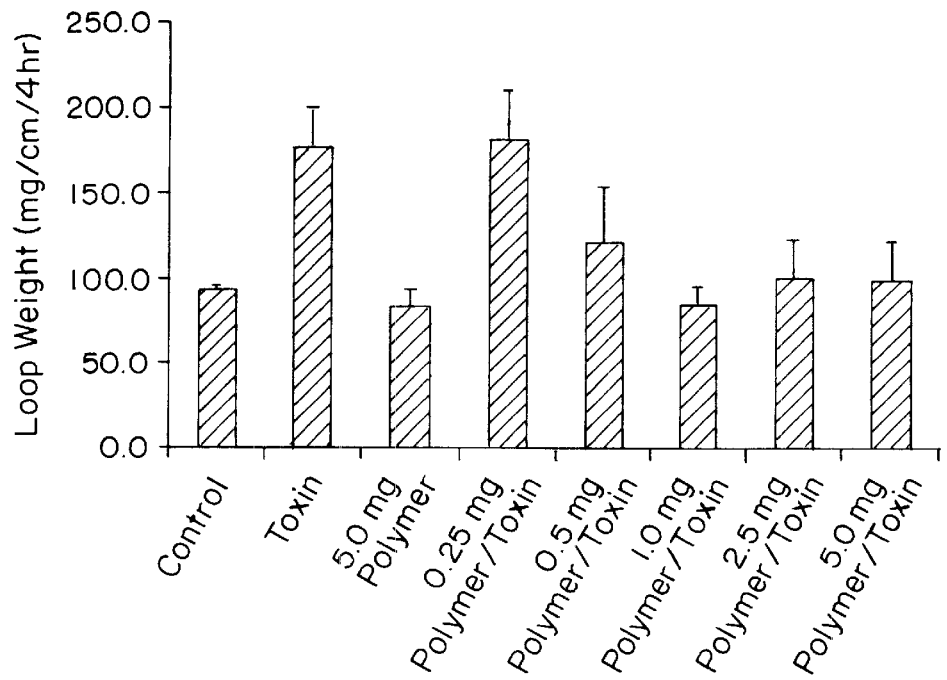
FIGS. 1 and 2 describe the effects of polystyrene sulfonate (160–246) on Toxin A in two hamster models, described in more detail below.
Figure 2:
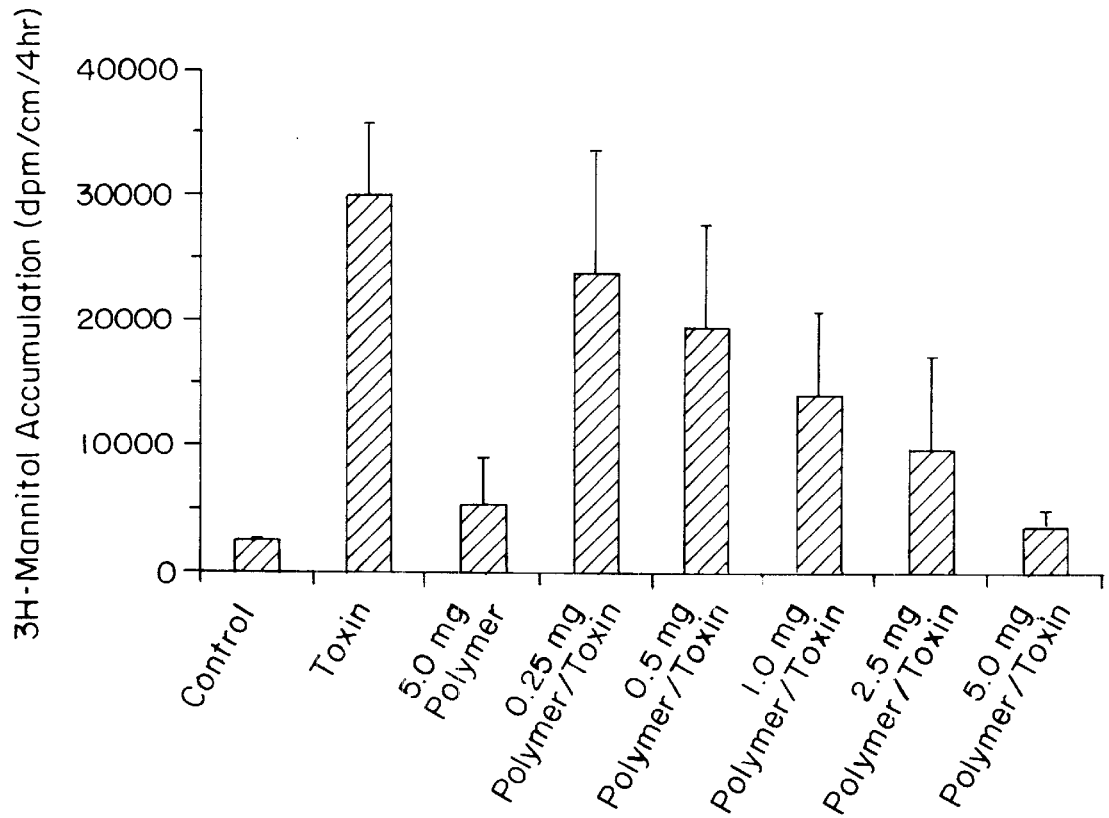

The present invention relates to a method of inhibiting a pathogenic or microbial toxin in a patient, such as a human, by administering to the patient a therapeutically effective amount of a polymer comprising a plurality of pendant acid functional groups. The acid functional group can be directly bonded to the polymer backbone or linked to the polymer backbone by an aliphatic spacer group having a length of from 1 to about 20 atoms.

As used herein the term "inhibiting a microbial toxin" refers to inhibiting the activity of a toxin which is associated with the development of a particular disease state or medical condition. The microbial toxin is an endotoxin or exotoxin produced by a microorganism, such as a bacterium, a fungus, a protozoan or a virus. The toxin can be inhibited by any mechanism, including, but not limited to, binding of the toxin by the polymer. As used herein, a "therapeutically effective amount" is an amount sufficient to inhibit or prevent, partially or totally, tissue damage or other symptoms associated with the action of the toxin within or on the body of the patient or to prevent or reduce the further progression of such symptoms.

The present invention provides methods and therapeutic compositions useful for treating AAD, including CDAD, and colitis. As used herein, the term "treating" diseases of the invention includes: prophylactic treatment of those mammals susceptible to AAD, CDAD or inflammatory colitis; treatment at the initial onset of AAD, CDAD or inflammatory colitis; treatment of ongoing AAD, CDAD or inflammatory colitis; and treatment of relapsing AAD, CDAD or inflammatory colitis in susceptible mammals. As used herein a "susceptible" mammal is a mammal capable of developing disease or having a relapse of disease for any reason including use of broad spectrum antibiotics which may disrupt the normal flora leading to CDAD. Therapeutic compositions of the invention preferably comprise polystyrene sulfonate, salts and copolymers therefor.

The term "monomer", as used herein, refers to both a molecule comprising one or more polymerizable functional groups prior to polymerization, and a repeat unit of a polymer. A copolymer is said to characterized by the presence of two or more different monomers.

As used herein, the term "polymer backbone" or "backbone" refers to that portion of the polymer which is a continuous chain comprising the bonds which are formed between monomers upon polymerization. The composition of the polymer backbone can be described in terms of the identity of the monomers from which it is a-formed, without regard to the composition of branches, or side chains, off of the polymer backbone. Thus, poly(acrylic acid) is said to have a poly(ethylene) backbone which is substituted with carboxylic acid (—C(O)OH) groups as side chains.

A "pendant" group is a moiety which forms a side chain or a portion of a side chain attached to the polymer backbone. A pendant group can, for example, be bonded directly to one or more atoms within the polymer backbone or can be connected to the polymer backbone by way of a spacer group.

The acid-functionalized monomer comprises a pendant acid functional group, such as a carboxylic acid group, a sulfonic acid group, a hydrosulfate group, a phosphonic acid group, a sulfamic acid group, a hydrophosphate group or a boronic acid group. Acid functional groups are referred to herein as the acid protonated form or partially protonated form. However, it is to be understood that any acid functional group can also exist in the conjugate base or deprotonated form in combination with a pharmaceutically acceptable cation. The polymer to be administered can include acid functional groups in either the protonated form, the deprotonated form or a combination thereof. Suitable cations include alkali metal ions, such as sodium, potassium and cesium ions, alkaline earth ions, such as calcium and magnesium ions, transition metal ions and unsubstituted and substituted (primary, secondary, tertiary and quaternary) ammonium ions. In one embodiment, the cation is a polyvalent metal ion, such as $Ca^{2+}$, $Mg^{2+}$, $Zn^{2+}$, $Al^{3+}$, $Bi^{3+}$, $Fe^{2+}$ or $Fe^{3+}$. It is preferred that the polymer is substantially free of acid anhydride groups. For example, less than 5%, preferably less than 2%. More preferably none of the acid functional groups within the polymer are present in the anhydride form.

The acid functional group can be directly bonded to the polymer backbone, or can be attached to the polymer backbone via a spacer group. The spacer group is a component of the polymer side chain and connects the acid functional group to the polymer backbone. The spacer group can be linear, branched or cyclic, aliphatic, aromatic or partially aromatic and partially aliphatic. Suitable aliphatic spacer groups include normal or branched, saturated or partially unsaturated hydrocarbyl groups, including alkylene groups, for example, polymethylene groups such as —$(CH_2)_n$—, wherein n is an integer from 1 to about 20, and cycloalkylene groups, such as the 1,4-cyclohexylene group. The alkylene group can be substituted or unsubstituted. Suitable alkylene substituents include hydroxyl groups and halogen atoms, for example, fluorine, chlorine and bromine atoms. The alkylene group can also, optionally, be interrupted at one or more points by a heteroatom, such as an oxygen, nitrogen or sulfur atom. Examples include the oxaalkylene groups, e.g. —$(CH_2)_2O[(CH_2)_2O]_n(CH_2)_2$—, wherein n is an integer ranging from 0 to about 3. The spacer group can also be a partially unsaturated group, such as a substituted or unsubstituted $C_2$–$C_{20}$-alkenylene group or a $C_2$–$C_2$-alkenylene group interrupted at one or more points by a heteroatom. Suitable aromatic spacer groups include ortho-, meta- and para-phenylene groups, naphthylene groups and biphenylene groups.

In one embodiment, at least a portion of the repeat units within the polymer further include a pendant hydrophobic group. The pendant hydrophobic group can be a substituted or unsubstituted, saturated or partially unsaturated $C_2$–$C_{24}$-hydrocarbyl group or a substituted or unsubstituted aryl or arylalkyl group. Examples of suitable alkyl substituents include halogen atoms, such as fluorine or chlorine atoms, and aryl groups, such as a phenyl group. Aryl substituents can include halogen atoms, $C_1$–$C_6$-alkyl groups and $C_1$–$C_6$-alkoxy groups. Preferably, the pendant hydrophobic group is a normal or branched $C_2$–$C_{24}$-alkyl group.

In one embodiment, the polymer to be administered is a homopolymer. In another embodiment, the polymer to be administered is a copolymer which is characterized by an acid-functionalized monomer and a hydrophobic monomer. The term "hydrophobic monomer", as used herein, is a monomer which comprises a pendant hydrophobic group, as described above. Suitable hydrophobic monomers include, but are not limited to, a substituted or unsubstituted N—$C_3$–$C_{24}$-alkylacrylamide, such as N-n-decylacrylamide and N-isopropylacrylamide; substituted or unsubstituted $C_3$–$C_{24}$-alkylacrylates, such as n-butylacrylate and n-decylacrylate; styrene and substituted styrenes, such as pentafluorostyrene and 4-fluorostyrene; vinylnaphthalene and vinylbiphenyl. The copolymer can have a wide range of compositions, comprising, for example, from about 10 mole % to about 50 mole % of the hydrophobic monomer, and from about 90 mole % to about 50 mole % of the acid-functionalized monomer.

In a preferred embodiment, the polymer to be administered is characterized by a repeat unit which comprises one acid functional group. In this embodiment, no two acid functional groups within the polymer will be connected to adjacent polymer backbone atoms. In one embodiment, the polymer to be administered is characterized by a repeat unit or monomer of the general formula

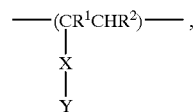

wherein X is a spacer group, as described above, or a direct bond, $R^1$ and $R^2$ are each, independently, hydrogen or an alkyl group, preferably methyl or ethyl, and Y is an acid functional group. Examples of suitable monomers of this type include acrylic acid, methacrylic acid, vinylsulfonic acid, vinylphosphonic acid, 3-allyloxy-2-hydroxy-1-propanesulfonic acid, vinylacetic acid and esters of vinyl alcohol and allyl alcohol with mineral acids, such as sulfuric, phosphoric and boric acids, including vinyl hydrosulfate, vinyl dihydrophosphate, allyl hydrosulfate, allyl dihydrophosphate and conjugate bases thereof. The monomer can also be polymerized alkene which is substituted with an acid functional group, such as undecenoic acid, undecenyl hydrosulfate and undecenyl sulfonic acid. Other suitable examples include acid-functionalized styrene, such as styrene sulfonate, styrene phosphonate and vinylbenzoic acid, acid-functionalized vinylnaphthalene, such as vinylnaphthalene sulfonate, and acid-functionalized vinylbiphenyl, such as vinylbiphenyl sulfonate.

In another embodiment, the polymer to be administered is characterized by a repeat unit or monomer of the general formula

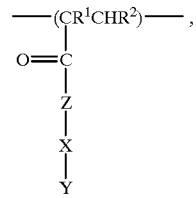

wherein Z is oxygen or NH and X is a spacer group, as described above, or a direct bond. Y is an acid functional group and $R^1$ and $R^2$ are each, independently, hydrogen or an alkyl group, preferably methyl or ethyl. Examples of suitable monomers of this type include 2-acrylamidoglycolic acid and 2-acrylamido-2-methyl-1-propanesulfonic acid.

Suitable copolymers for use in the present method include copolymers of acrylic acid and a $C_2$–$C_{20}$-alkylacrylate, such as poly(acrylic acid-co-n-decylacrylate) and poly(acrylic acid-co-n-butylacrylate). Also included are copolymers of acrylic acid and an N—$C_2$–$C_{20}$ alkylacrylamide, such as poly(acrylic acid-co-N-isopropylacrylamide) and poly (acrylic acid-co-N-n-decylacrylamide), and copolymers of acrylic acid with styrene or a substituted styrene, such as pentafluorostyrene or 4-fluorostyrene.

In another embodiment, the polymer to be administered is a copolymer comprising an acid-functionalized monomer, a hydrophobic monomer and a neutral hydrophilic monomer. A neutral hydrophilic monomer is a monomer comprising a polar group which is neither appreciably acidic nor appreciably basic at physiological pH. Examples of suitable neutral hydrophilic monomers include acrylamide, N-(2-hydroxyethyl) acrylamide, N-(3-hydroxypropyl)acrylamide, 2-hydroxyethylacrylate, vinyl acetate, vinyl alcohol and N-vinylpyrrolidone. A suitable copolymer of this type is the terpolymer poly(acrylic acid-co-n-decylacrylate-co-acrylamide).

The polymer to be administered can also be characterized by a repeat unit comprising both a pendant hydrophobic group and a pendant acid functional group. Suitable hydrophobic groups and acid functional groups include those discussed above. Polymers of this type include poly(2-alkylacrylic acid), wherein the alkyl group comprises from 2 to about 24 carbon atoms. One suitable polymer of this type is poly(2-ethylacrylic acid) or a conjugate base thereof. The polymer to be administered can also comprise a first monomer having a pendant hydrophobic group and a pendant acid functional group and a second neutral, hydrophilic monomer, such as the neutral hydrophilic monomers previously discussed.

In one embodiment, the polymer to be administered comprises a first repeat unit which comprises a pendant acid functional group and a second repeat unit which comprises a pendant acid derivative, such as an amide group or an ester group. Suitable examples of polymers of this type include poly(styrenesulfonate) in which a portion of the sulfonate groups have been converted to sulfonamide or sulfonate ester groups and polyacrylate in which a portion of the carboxylate groups have been converted to amide or ester groups. The properties of the polymer can be varied by varying the amount and chemical features of the groups introduced into the polymer via the amidation or esterification process. In one embodiment, the polymer comprises repeat units having pendant ester groups, where the ester group is derived from an alcohol, such as menthol, a bile acid, such as cholic acid or lithocholic acid, or an alkanol, such as a normal or branched $C_4$–$C_2$-alkanol. In another embodiment, the polymer comprises repeat units having pendant amide groups, where the amide groups are derived from an amine, such as an alkylamine, for example, a normal or branched $C_4$–$C_2$-alkylamine or an ammonioalkylamine. Suitable ammonioalkylamines include compounds of the formula $R^1(R^2)(R^3)N^+(CH_2)_nNH_2$, where $R_1$, $R_2$ and $R_3$ are each, independently, hydrogen, a $C_1$–$C_2$-alkyl group or an arylalkyl group, and n is an integer from 1 to about 12.

In another embodiment, the polymer to be administered is a copolymer comprising an acid-functionalized monomer or repeat unit, a cationic repeat unit and, optionally, a hydrophobic repeat unit and/or a neutral hydrophilic repeat unit. For example, the acid-functionalized, hydrophobic and neutral hydrophilic repeat unit can include any of the repeat units of these types discussed above. The cationic repeat unit carries a positive charge under physiological conditions, and, preferably, includes a pendant amino or ammonium group. Suitable repeat units of this type include those disclosed in U.S. patent application Ser. No. 08/934,495, incorporated herein by reference n its entirety. Examples of suitable cationic repeat units include allylamine, N-substituted allylamine, quaternized allylamine, diallylamine, N-substituted diallylamine, quaternized diallylamine, vinylamine, N-substituted vinylamine, quaternized vinylamine, N-aminoalkylacrylamide and -methacrylamide, N-ammonioalkylacrylamide and -methacrylamide, aminoalkyacrylate and -methacrylate, and ammonioalkylacrylate and -methacrylate. The ratio of anionic and cationic repeat units can vary widely, for example, from about 95% anionic monomer and 5% cationic monomer relative to the total charged monomers in the polymer, to about 5% anionic monomer and 95% cationic monomer relative to the total charged monomers, preferably 75% or more of the monomers are anionic.

Preferred polymers of the invention include but are not limited to:

Poly(vinylsulfate), poly(propenesulfate), poly(butenesulfate), poly(pentenesulfate), poly(hexenesulfate), poly(heptenesulfate), poly(octenesulfate), poly(nonenesulfate), poly(decenesulfate), poly(undecenesulfate), poly(dodecenesulfate)

Poly(vinylsulfonate), poly(propenesulfonate), poly(butenesulfonate), poly(pentenesulfonate), poly(hexenesulfonate), poly(heptenesulfonate), poly(octenesulfonate), poly(nonenesulfonate), poly(decenesulfonate), poly(undecenesulfonate), poly(dodecenesulfonate)

Poly(vinylphosphate), poly(propenephosphate), poly(butenephosphate), poly(pentenephosphate), poly(hexenephosphate), poly(heptenephosphate), poly(octenephosphate), poly(nonenephosphate), poly(decenephosphate), poly(undecenephosphate), poly(dodecenephosphate)

Poly(vinylphosphonate), polypropenephosphonate), poly(butenephosphonate), poly(pentenephosphonate), poly(hexenephosphonate), poly(heptenephosphonate), poly(octenephosphonate), poly(nonenephosphonate), poly(decenephosphonate), poly(undecenephosphonate), poly(dodecenephosphonate)

Carrageenan, heparin, heparan sulfate, dextran sulfate, pentosan sulfate, laminarin sulfate, chondroitin sulfate, dermatan sulfate Poly(styrenesulfonate), poly(styrenesulfate), poly(styrenesulfanilate), poly(sulfophenylalanine), poly(tyrosinesulfate), poly(sulfophenethylacrylamide), poly(sulfophenethylmethacrylamide), poly(vinylnaphthalenesulfonate), poly(vinylnaphthalenesulfate), poly(vinylbiphenylsulfonate), poly(vinylbiphenylsulfate), poly(anetholesulfonate), poly(vinylbenzoic acid)

Poly(sulfophenylpropene), poly(sulfophenylbutene), poly(sulfophenylpentene), poly(sulfophenylhexene), poly(sulfophenylheptene), poly(sulfophenyloctene), poly(sulfophenylnonene), poly(sulfophenyldecene), poly(sulfophenylundecene), poly(sulfophenyldodecene)

Poly(sulfatephenylpropene), poly(sulfatephenylbutene), poly(sulfatephenylpentene), poly(sulfatephenylhexene), poly(sulfatephenylheptene), poly(sulfatephenyloctene), poly(sulfatephenylnonene), poly(sulfatephenyldecene), poly(sulfatephenylundecene), poly(sulfatephenyldodecene)

Poly(phosphophenylpropene), poly(phosphophenylbutene), poly(phosphophenylpentene), poly(phosphophenylhexene), poly(phosphophenylheptene), poly(phosphophenyloctene), poly(phosphophenylnonene), poly(phosphophenyldecene), poly(phosphophenylundecene), poly(phosphophenyldodecene)

Poly(phosphatephenylpropene), poly(phosphatephenylbutene), poly(phosphatephenylpentene), poly(phosphatephenylhexene), poly(phosphatephenylheptene), poly(phosphatephenyloctene), poly(phosphatephenylnonene), poly(phosphatephenyldecene), poly(phosphatephenylundecene), poly(phosphatephenyldodecene)

Sulfonated poly(vinylphenyl ketone), sulfonated poly(phenylsulfone), sulfonated poly(4-methylstyrene), sulfonated poly($\alpha$-methylstyrene), sulfonated poly(styrene-block-ethyleneoxide-block-styrene), sulfonated poly(ethylene oxide-block-styrene-block-ethyleneoxide), sulfonated poly(4-methoxystyrene), sulfonated poly(diphenoxypbosphazene), sulfonated poly(ethyleneoxide-block-styrene), sulfonated poly(styrene-block-ethylene), sulfonated poly(acenaphthylene), sulfonated poly(vinylcarbazole), sulfonated poly(styrene-co-butadiene), sulfonated poly(styrene-block-(ethylene-co-butylene)-block-styrene)

Poly(styrenesulfonate-co-maleic acid), poly(styrenesulfonate-co-acrylic acid), poly(styrenesulfonate-co-methacrylic acid), poly(styrenesulfonate-co-acrylamidomethylpropanesulfonate), poly(styrenesulfonate-co-itaconic acid), poly(styrenesulfonate-co-vinylbenzoic acid)

Poly(styrenesulfonate-co-diallylmethylammonium chloride), poly(styrenesulfonate-co-diallyldimethylammonium chloride), poly(styrenesulfonate-co-diallylmethyloctylammonium chloride), poly(styrenesulfonate-co-allylamine), poly(styrenesulfonate-co-vinylamine), poly(styrenesulfonate-co-vinylbenzyltrimethylammonium chloride)

Poly(styrenesulfonate-co-styrene), poly(styrenesulfonate-co-octylstyrenesulfonamide), poly(styrenesulfonate-co-menthylstyrenesulfonate), poly(styrenesulfonate-co-lithocholic acid styrenesulfonate), The polymers of use in the present method can be linear or crosslinked. The polymer can be crosslinked, for example, by the incorporation within the polymer of a multifunctional comonomer. Suitable multifunctional co-monomers include diacrylates, triacrylates and tetraacrylates, dimethacrylates, diacrylamides, diallylacrylamide, di(methacrylamides), triallylamine and tetraalkylammonium ion. Specific examples include ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), pentaerythritol tetraacrylate, trimethylolpropane triacrylate, bisphenol A dimethacrylate, and bisphenol A diacrylate. Other suitable multifunctional monomers include polyvinylarenes, such as divinylbenzene. The amount of crosslinking agent is typically between about 1.0% and about 30% by weight relative to the weight of the polymer, preferably from about 5% to about 25% by weight.

The polymer can also be cross-linked subsequent to polymerization. For example, a portion of the acid functional groups can be converted to a reactive derivative, as is known in the art. For example, carboxylic acid and sulfonic acid groups react with thionyl chloride to produce, respectively, acyl chloride and sulfonyl chloride groups. These reactive groups can then be reacted with a diamine, a dialcohol or an amino alcohol, preferably diamine, a dialcohol or an amino alcohol in which the amino and/or hydroxyl groups are separated by an alkylene chain, such as a $C_3$–$C_{18}$-alkylene chain. This reaction results in the formation of ester and/or amide groups on a given polymer chain which are linked to similar groups on adjacent polymer chains. The extent of cross-linking can be controlled, for example, by controlling the fraction of acid functional groups which are converted to reactive groups.

The molecular weight of the polymer is not critical, but is, preferably, suitable for the intended mode of administration and allows the polymer to reach and remain within the targeted region of the body. For example, a method for treating an intestinal infection should utilize a polymer of sufficiently high molecular weight or degree of cross-linking to resist absorption, partially or completely, from the gastrointestinal tract into other parts of the body. Preferably, if linear, the polymer to be administered has a molecular weight ranging from about greater than 1 to about 1 million Daltons or more, such as 2,000 Daltons to about 500,000 Daltons, 5,000 Daltons to about 150,000 Daltons, or about 25,000 Daltons to about 1 million Daltons. Alternatively, the molecular weight can be from about 100,000 to about 1 million or between about 400,000 to about 1 million Daltons. The polymers of use in the present method are preferably substantially nonbiodegradable and nonabsorbable. That is, the polymers do not substantially break down under physiological conditions into fragments which are absorbable by body tissues. The polymers preferably have a nonhydrolyzable backbone, which is substantially inert under conditions encountered in the target region of the body, such as the gastrointestinal tract. A particularly preferred polymer is polystyrene sulfonate. Preferably, the polymer is a soluble, uncrosslinked polystyrene sulfonate polymer having a molecular weight between about 400,000 and 1 million Daltons, such as 600,000 Daltons. Alternatively, polymer backbones which are suitable for the present invention include polyacrylamide, polyacrylate, poly(vinyl) and poly(ethyleneimine), polystyrene backbones. A co-polymer of the present invention can comprise a combination of two or more of these backbone elements. The polymer to be administered can also be an condensation polymer, such as a polyamide or a polyester.

The quantity of a given polymer to be administered will be determined on an individual basis and will be determined, at least in part, by consideration of the individual's size, the identity of the known or suspected pathogenic organism, the severity of symptoms to be treated and the result sought. The polymer can be administered alone or in a pharmaceutical composition comprising the polymer and one or more pharmaceutically acceptable carriers, diluents or excipients. The pharmaceutical composition can also, optionally, include one or more additional drugs, such as antibiotics, anti-inflammatory agents or analgesics.

The polymer can be administered by subcutaneous or other injection, intravenously, topically, orally, parenterally, transdermally, or rectally through feeding tube. Preferably, the polymer or the pharmaceutical composition comprising the polymer is administered orally. The form in which the polymer is administered, for example, powder, tablet, capsule, solution, or emulsion, will depend on the route by which it is administered. The therapeutically effective amount can be administered in a single dose or in a series of doses separated by appropriate time intervals, such as hours.

For oral delivery, polymers may be administered at a doseage of about 0.1 to 10 g/Kg/day and more preferably from 1.0 –7.0 g/Kg/day and even more preferably from 2.0 to 6.6 g/Kg/day.

The polymer can also administered in combination with one or more antimicrobial agents, for example, selected from among antibiotics which are known in the art. The antibiotic to be administered is, generally, selected based on the identity or suspected identity of the pathogenic microorganism, as is known in the art. For example, if the pathogenic microorganism is *C. parvum,* one suitable antibiotic which can be administered in combination with the polymer is paromomycin. The polymer and the antimicrobial agent can be administered simultaneously, for example, in separate dosage forms or in a single dosage form, or in sequence separated by appropriate time intervals.

The term "antimicrobial agent" is intended to include antibacterial agents, antifungal agents, antiseptics and the like. Suitable antimicrobial agents are known in the art and include isoniazid, rifampin, pyrazinamide, ethambutol, erythromycin, vancomycin, tetracycline, chloramphenicol, sulfonamides, gentamicin, amoxicillin, penicillin, streptomycin, p-aminosalicyclic acid, clarithromycin, clofazimine, minocycline, sulfonamides, ethionamide, cycloserine, kanamycin, amikacin, capreomycin, viomycin, thiacetazone, rifabutin and the quinolones, such as ciprofloxacin, ofloxacin and sparfloxicin. The term "antibacterial agent" includes but is not limited to: naturally occurring antibiotics produced by microorganisms to suppress the growth of other microorganisms, and agents synthesized or modified in the laboratory which have either bactericidal or baceriostatic activity, e.g., β-lactam antibacterial agents including, e.g. carbencillim; ampicillin, cloxacillin, oxacillin and pieracillin, cephalosporins and other cephems including, e.g. cefaclor, cefamandole, cefazolin, cefoperazone, ceftaxime, cefoxitin, ceftazidime, ceftriazone and carbapenems including, e.g., imipenem and meropenem; and glycopeptides, macrolides, quinolones (e.g. nalidixic acid), tetracyclines, aminoglycosides (e.g. Gentamicin and Paromomycin) and further includes antifungal agents. In general if an antibacterial agent is bacteriostatic, it means that the agent essentially stops bacterial cell growth (but does not kill the bacteria); if the agent is bacteriocidal, it means that the agent kills bacterial cells (and may stop growth before killing the bacteria).

Thus, the polymers and compositions described herein can be used in medicine, for example, in the manufacture of a medicament for the therapies and treatments described herein.

In one embodiment, the polymer which comprises a plurality of pendant acid functional groups is administered in combination with a cationic polymer, preferably a polymer comprising amino and/or ammonium groups. Examples of suitable polymers of this type are disclosed in copending application Ser. No. 08/934,495, incorporated herein by reference in its entirety. Suitable cationic polymers can be linear or cross-linked. Included are polymers comprising repeat units or monomers such as allylamine, diallylamine, diallylmethylamine, vinylamine, N-aminoalkylacrylamide, N-aminoalkylmethacrylamide, aminoalkylacrylate, aminoalkylmethacrylate and acid addition salts and monoalkylated, dialkylated and trialkylated (quaternized) derivatives thereof. Suitable cationic polymers include homopolymers of these repeat units and copolymers including at least one of these repeat units and, optionally, one or more hydrophobic monomers and/or neutral hydrophilic monomers, as discussed above. The acid-functionalized polymer and the cationic polymer can be administered in varying ratios by weight and can be administered simultaneously, for example, in a single dosage form or in separate dosage forms, or in a sequence separated by minutes or hours. Suitable dosages and administration methods can be readily determined by one of skill in the art. In one embodiment, the anionic polymer is poly(styrensulfonate) and the cationic polymer is poly(diallylmethylamine) or poly(diallylmethylamine) in which a portion of the repeat units have been alkylated, for example with a $C_4$–$C_2$-alkyl group, such as an octyl group or a decyl group.

The polymers of the present invention can be prepared via methods known in the art, for example, by direct polymerization of an acid-functionalized monomer or copolymerization of a monomer mixture comprising an acid-functionalized monomer and at least one additional co-monomer, such as a second acid-functionalized monomer, a hydrophobic monomer, a neutral hydrophilic monomer, a multifunctional cross-linking monomer or a combination thereof The monomer mixture can be polymerized using, for example, methods of free radical, cationic or anionic polymerization which are well known in the art. Due to differences in the reactivity ratios of two or more monomers, the mole ratio of the monomers in the copolymer product can be different from the mole ratio of the monomers in the initial reaction mixture. This reactivity difference can also result in a non-random distribution of monomers along the polymer chain.

The polymers can also be synthesized by nucleophilic side chain substitution on a activated polymer. This method proceeds via an intermediate polymer having labile side chains which are readily substituted by a desired side chain. Suitable polymers of this type include poly(N-acryloyloxysuccinimide) (pNAS), which reacts with a primary amine, for example, to form an N-substituted polyacrylamide. Another suitable polymer with labile side chains is poly(4-nitrophenylacrylate), which also forms an N-substituted polyacrylamide upon reaction with a primary amine.

For example, a copolymer with a polyacrylamide backbone comprising amide nitrogen atoms substituted with an acid functional group and amide nitrogen atoms substituted with a hydrophobic group can be prepared by treating pNAS with less than one equivalent (relative to N-acryloyloxysuccinimide monomer) of a primary amine which terminates in an acid functional group, such as an amino acid, for example, glycine. A hydrophobic group can then be introduced by reacting at least a portion of the remaining N-acryloyloxysuccinimide monomers with a second primary amine, such as a $C_2$–$C_{20}$-alkylamine. A co-polymer further comprising a neutral hydrophilic monomer can be prepared by reacting any remaining N-acryloyloxysuccinimide monomers with, for example, 2-aminoethanol or ammonia. A variety of copolymer compositions can, thus, be readily obtained by treating the activated polymer with different ratios of selected amines.

The polymers of use in the present method can also be synthesized by functionalization of a precursor polymer with an acid functional group. For example, a polymer having side chains which include aryl groups can be sulfonated using known methods to produce a polymer having pendant sulfonic acid groups. Precursor polymers which include hydroxyl groups, such as poly(vinyl alcohol) and poly(allyl alcohol) can be sulfated using known methods to form polymers comprising sulfate ester groups. Polymers having both acid functional groups and hydrophobic groups can also be synthesized using this general approach. For example, a poly(vinylarene) polymer, such as polystyrene can be sulfonated by reaction with, for example, fuming sulfuric acid, to form poly(styrene sulfonate).

An acid-functionalized polymer can be modified by converting at least a portion of the acid groups to an acid derivative, such as an amide or an ester. For example, poly(styrenesulfonate) can be reacted with a substoichiometric amount, based on sulfonate groups, of thionyl chloride, thereby converting a portion of the sulfonate groups to sulfonyl chloride groups. The resulting polymer can, for example, be reacted with an excess of a primary amine to convert the sulfonyl chloride groups to N-substituted-sulfonamide groups or with an alcohol to convert the sulfonyl chloride groups to sulfonate ester groups. The hydrophobicity of the resulting polymer can be varied by varying either or both of the N-substituent or ester functionality and the extent of conversion of sulfonate groups to sulfonamide or sulfonate ester groups.

Pathogenic toxins which can be inhibited by the method of the present invention include, but are not limited to, toxins, such as exotoxins and/or endotoxins produced by Streptococcus spp., including *Streptococcus pneumoniae, Streptococcus pyogenes* and *Streptococcus Sanguis*; Salmonella spp., including *Salmonella enteritidis*; Campylobacter spp., including *Campylobacter jejuni*; Escherichia spp., including *E. coli;* Clostridia spp., including *Clostridium diffile* and *Clostridium botulinum*; Staphylococcus spp., including *Staphylococcus aureus;* Shigella spp., including *Shigella dysenteriae;* Pseudomonas spp., including *Pseudomonas aeruginosa;* Bordatella spp., including *Bordatella pertussis;* Listeria spp., including *Listeria monocytogenes; Vibro cholerae;* Yersinia spp., including *Yersinia enterocolitica;* Legionella spp., including *Legionella pneumophilia;* Bacillus spp., including *Bacillus anthracis;* Helicobacter spp.; Corynebacteria spp.; Actinobacillus spp.; Aeromonas spp.; Bacteroides spp. including Bacteroidesfragilis; Neisseria spp, including *N. meningitidis;* Moraxella spp., such as *Moravella catarrhalis* and Pasteurella spp.. Also included are protozoal toxins, such as toxins produced by *Entameoba histolytica* and Acanthameoba; and parasitic toxins.

The method of the invention can also be used to inhibit a viral toxin, such as a toxin produced by rotavirus, human immunodeficiency virus, influenza virus, polio virus, vesicular stomatitis virus, vaccinia virus, adenovirus, piavirus, togaviruses (such as sindbis and semlikifores viruses), paramyxoviruses, papillomaviruses. Toxins which can be inhibited using the method of the invention include viroporin molecules produced by any of these viruses. A preferred toxin which can be inhibited using the method of the invention is the rotavirus NSP4 protein. Other toxins which can be inhibited include influenza M2 protein, HIV Vpu and gp4l proteins, picomavirus 3A protein, togavirus 6K protein, respiratory syncitial virus SH protein, coronavirus D3 protein and adenovirus E5 protein.

The infection can be a systemic infection or a localized infection. Preferably, the infection is localized to one or more of the oral cavity, the eye, the gastrointestinal tract, including the throat, the skin and the ear, such as the ear canal or the middle ear.

The quantity of a given polymer to be administered will be determined on an individual basis and will be determined, at least in part, by consideration of the individual's size, the severity of symptoms to be treated and the result sought. The polymer can be administered alone or in a pharmaceutical composition comprising the polymer, an acceptable carrier or diluent and, optionally, one or more additional drugs.

The polymer can be administered systemically or non-systemically, for example, by subcutaneous or other injection, intravenously, topically, orally, parenterally, transdermally, or rectally. The route of administration selected will generally depend upon whether the infection is systemic or localized The form in which the polymer will be administered, for example, powder, tablet, capsule, solution, or emulsion, will depend on the route by which it is administered. The therapeutically effective amount can be administered in a series of doses separated by appropriate time intervals, such as hours. Preferably, the polymer is administered non-systemically, for example, orally or topically, for example, by application to the skin, the eye, oral tissue, such as the oral mucosa, or gastrointestinal mucosa.

In a preferred embodiment, the toxin is an exotoxin produced by a pathogenic bacterial strain. Of particular pathogenic importance are *Escherichia coli,* for example, *E. coli* strains 06:H-, 0157:H7, 0143 and other clinical isolates, and *Clostridium difficile.* Enterohemorrhagic *E. coli* (EHEC), such as 0157:H7, can cause a characteristic non-febrile bloody diarrhea known as hemorrhagic colitis. EHEC produce high levels of one or both of two related cytotoxins which resemble a Shiga toxin in structure and function and are referred to as Shiga-like toxins (SLT I or SLT II). These Shiga-like toxins are believed to damage the intestinal mucosa, resulting in the manifestation of hemorrhagic colitis.

In a preferred embodiment, the microbial toxin or toxins are produced by *Clostridium difficile. C. difficile* produces two toxins, Toxin A and Toxin B. Toxin A is an enterotoxin which stimulates infiltration of neutrophils and release of mediators of inflammation, resulting in fluid secretion, altered membrane permeability and hemorrhagic necrosis. Toxin B is a cytotoxin. *C. difficile* is associated with many cases of antibiotic-associated diarrhea and most cases of pseudomembranous colitis, a severe, potentially fatal inflammation of the colon. Treatment of *C. difficile* infection typically involves administration of vancomycin or metronidazole. In one embodiment, the condition to be treated is *C. difficile* induced gastroenteritis, such as antibiotic-associated diarrhea or pseudomembranous colitis. In this embodiment, the polymer can, optionally be administered in combination with one or more antibiotic agents which are effective, at least partially, against *C. difficile,* such as vancomycin and metronidazole.

As used herein "treatment" of *C. difficile* associated diarrhea (CDAD) includes: prophylactic treatment of those patients susceptible to CDAD; treatment at initial onset of CDAD; treatment of ongoing CDAD and treatment of relapsing CDAD in susceptible patients. As used herein a "therapeutically effective amount" is an amount sufficient to prevent, diminish or eradicate symptoms of disease.

In a preferred embodiment, a therapeutic/prophylactic CDAD treatment regimen (which results in prevention of disease, diminution or eradication of disease after onset, or prevention of relapse of disease) comprises administration of a therapeutically effective amount of a therapeutic composition comprising polystyrene sulfonate, preferably soluble, uncrosslinked polystyrene sulfonate and even more preferably, soluble, uncrosslinked polystyrene sulfonate having a molecular weight of between 400,000 and 1 million, and most preferably a molecular weight of 600,000. While not intending to be limited to any mechanism, compositions in accordance with the invention bind the toxins, e.g. toxins produced by *C. difficile* . Toxin A is an enterotoxin which stimulates infiltration of neutrophils and release of mediators of inflammation, resulting in fluid secretion, altered membrane permeability and hemorrhagic necrosis. Toxin B is a cytotoxin. These toxins are believed to be responsible for the symptoms of CDAD and other AAD.

The present invention also contemplates a prophylactic treatment regimen comprising administering a therapeutic composition comprising polystyrene sulfonate as a cotherapy with broad spectrum antibiotic therapy. As used herein "cotherapy" means a treatment regiment wherein two drugs are administered simultaneously or sequentially, separated by minutes, hours or days, but in some way act together to provide the desired therapeutic response.

The invention will now be further and specifically described by the following examples.

EXAMPLES

Example 1

Synthesis of Acrylic Acid/Styrene Copolymer (2:1)

A solution was prepared of acrylic acid (15.0 g, 0.2 mol) and styrene (10.4 g, 0.1 mol) in THF (200 mL). After the solution was degassed with a rapid stream of nitrogen, azobisisobutyronitrile (AEBN) (1.47 g, 3 mol % with respect to total monomer) was added.. The solution was degassed for a further thirty minutes and the reaction was then heated to 70° C. for 14 h. The solution was cooled and precipitated into n-hexane (800 mL). The hexane was decanted from the fibrous white product, the product was washed with ethyl acetate (300 mL) followed by washing with a further aliquot of hexane (200 mL). The polymer was dried in vacuo to yield 21.6 g, 84.6% of a brittle white solid.

Example 2

Synthesis of Acrylic Acid/Decylacrylate (96:4) Copolymer

A solution was prepared of acrylic acid (10.0 g, 133 mmol) and n-decylacrylate (1.0 g, 4.71 mmol) in dioxane (200 mL). The solution was degassed by passing a rapid stream of nitrogen through it, and to the solution was added AIBN (0.6 g, 5 mol % with respect to total monomer). The solution was degassed for a further thirty minutes and the reaction was then heated to 70° C. for 16 hr. The solution was cooled and precipitated into ethyl acetate (600 mL). The ethyl acetate was decanted from the fibrous white product, the product was washed with ethyl acetate (300 mL) and then with hexane (200 mL). The polymer was dried in vacuo to yield 9.0 g, 81% of a brittle white solid.

Example 3

Synthesis of Acrylic Acid/n-butylacrylate (9:1) Copolymer

A solution was prepared of acrylic acid (10.0 g, 133 mmol) and n-butylacrylate (2.0 g, 14.41 mmol) in dioxane (200 mL). The solution was degassed by passing a rapid stream of nitrogen through it, and to the solution was added AIBN (0.6 g, 5 mol % with respect to total monomer). The solution was degassed for a further thirty minutes and the reaction was then heated to 70° C. for 17 h. The solution was cooled and precipitated into ethyl acetate (600 mL). The ethyl acetate was decanted from the fibrous white product, the product was washed with ethyl acetate (300 mL) followed by washing with hexane (200 mL). The polymer was dried in vacuo to yield 9.0 g (81%) of a brittle white solid.

The corresponding copolymer of acrylic acid and n-butylacrylate (10:3) was made by the same procedure.

Example 4

Synthesis of Acrylic Acid/n-decylacrylate/ Acrylamide (70:7.5:22.5) terpolymer

A solution was prepared of acrylic acid (10.0 g, 133 mmol), n-decylacrylate (3.0 g, 14.2 mmol) and acrylamide (3.0 g, 42.2 mmol) in dioxane (200 mL). After the solution was degassed with a rapid stream of nitrogen, AIBN (1.3 g) was added. The solution was degassed for a further thirty minutes and the reaction was then heated to 70° C. for 17 h. The polymer precipitated as a fibrous white solid as the reaction proceeded. The solution was cooled and the dioxane decanted. The residue was washed with ethyl acetate (600 mL) and the ethyl acetate was discarded. The polymer was finally washed with hexanes (300 mL) and dried in vacuo.

Example 5

Synthesis of Acrylic Acid/n-butylacrylate/ Acrylamide (60:15:25) terpolymer

A solution was prepared of acrylic acid (10.0 g, 133 mmol), n-butylacrylate (4.0 g, 31.4 mmol) and acrylamide (4.0 g, 56.3 mmol) in dioxane (200 mL). After the solution was degassed with a rapid stream of nitrogen, AIBN (1.3 g) was added. The resulting solution was degassed for a further thirty minutes and was then heated to 70° C. for 17 h. As the reaction proceeded, the polymer precipitated as a white fibrous solid. The solution was cooled and the dioxane was decanted. The polymer was washed with ethyl acetate (600 mL), then with hexanes (300 mL) and dried in vacuo.

Example 6

Synthesis of Co-polymer of Acrylic Acid and Decylacrylate (10:2)

A solution was prepared of acrylic acid (10.0 g, 133 mmol) and decylacrylate (5.64 g, 26.6 mmol) in dioxane (300 mL). After the solution was degassed with a rapid stream of nitrogen, AIBN (0.8 g) was added. The resulting solution was degassed for a further thirty minutes and the reaction mixture was heated to 70° C. for 16 hr. The solution was cooled and added to ethyl acetate (600 mL). The ethyl acetate was decanted from the resulting fibrous white product. The product was then redissolved in dioxane (150 mL), precipitated with ethyl acetate (500 mL), filtered, washed with cold hexanes (300 mL) and dried in vacuo.

Example 7

Preparation of 2% Cross-linked poly (ethyleneglycolmethacrylate phosphate) Gel

Poly(ethyleneglycolmethacrylate phosphate) gel was prepared by polymerizing ethyleneglycolmethacrylate phosphate (29.4 mmoles, 6.178 g) with divinylbenzene ("DVB") (0.926 mmoles, 0.1319 mL) in ethanol/water (50/50) using about 1 mole % AIBN as initiator. The resulting resilient gel was split in 2 portions in two 50 mL centrifuge tubes and washed 4 times with ethanol for a total of about 120 mL of ethanol. The gel was dried overnight in a forced-air oven at 70° C. The dried gel was ground and sieved and washed 3 times in water in a 50 mL centrifuge tube. The gel was dried overnight in a forced-air oven at 70° C.

Example 8

Preparation of Sulfonated Polystyrene Gels

Polystyrene gels were prepared by polymerizing styrene with divinyl benzene in toluene using about 1 mole % AIBN as initiator as follows:

Polystyrene gel (6% DVB). Styrene (282 mmole, 3.23 mL) was added to a 40 mmL vial fitted with a septum cap. Toluene (5 mL) was added and the solution was degassed for 15 min. A solution of AIBN (0.9852 g in 10 mL of toluene) was prepared and 0.5 mL was added to the solution. The solution was further degassed for 5 min and then maintained at 60° C. for 21 hr. The resulting clear colorless gel was washed 5 times with ethanol in a 50 mL centrifuge tube and dried overnight in a 70° C. forced air oven.

Polystyrene gels were also prepared using this procedure with the following cross-linking levels: 4% DVB; 2% DVB; 1.5% DVB; 1% DVB; and 0.5% DVB.

Sulfonation of Polystyrene Gel

Dried polystyrene gel was transferred to a 40 mL glass vial. Concentrated sulfuric acid (10 mL) was added and the mixture was heated at 100° C. for 1 hr. The resulting brown, swollen gel was allowed to cool to room temperature and was washed exhaustively with methanol until the pH was 4–5. The gel was dried overnight in a 70° C. forced air oven. The dried gel was then ground in a coffee grinder, transferred to a 50 mL centrifuge tube, and washed several times with water.

Example 9

Preparation of Sulfonated poly(2-vinylnaphthalene) Gels

Poly(2-vinylnaphthalene) gels were prepared by polymerizing 2-vinyl-naphthalene with divinyl benzene in toluene using ~1 mole % AIBN as initiator as follows.

Poly(2-vinyl naphthalene) Gel (2% DVB)

2-Vinylnaphthalene (29.4 mmoles, 4.534 g) and divinylbenzene (0.6 mmoles, 85.46 microL) was added to a 40 mL vial fitted with a septum-cap. Toluene (10 mL) was added and the solution was heated to dissolve the monomer. The solution was degassed for 15 min. A solution of AIBN (0.9852 g in 10 mL in toluene) was prepared and 0.5 mL was added to the polymerization solution. The solution was further degassed for 5 min and then maintained at 60° C. for 21 h. The resulting clear brown gel was washed with ethanol (2 L total) by gravity filtration and dried for 2 days in a 70° C. forced air oven.

Sulfonation of poly(2-vinylnaphthalene) Gel

Dried poly(2-vinyl naphthalene) gel was transferred to a 40 mL glass vial. Concentrated sulfuric acid (10 mL) was added and the mixture was heated at 100° C. for 1 h. The resulting brown, swollen gel was allowed to cool to room temperature and was washed exhaustively with methanol by gravity filtration until the pH was 4–5. The gel was washed several times with water. The gel was dried for 2 days in a 70° C. forced air oven.

Example 10

Preparation of Sulfonated poly(4-vinylbiphenyl) Gels

Poly(4-vinylbiphenyl) gels were prepared by polymerizing 4-vinylbiphenyl with divinyl benzene in toluene using ~1 mole % AIBN as initiator as follows:

Poly(4-vinylbiphenyl) Gel (2% DVB)

4-Vinylbiphenyl (29.4 mmoles, 5.299 g) and divinylbenzene (0.6 mmoles, 85.46 microL) were added to a 40 mL vial fitted with a septum cap. Toluene (10 mL) was added and the solution was heated to dissolve the monomer. The solution was degassed for 15 min. A solution of AIBN (0.9852 g in 10 mL of toluene) was prepared and 0.5 mL was added to the polymerization solution. The solution was further degassed for 5 minutes and then maintained at 60° C. for 21 h. The resulting clear brown gel was washed with ethanol (2 L total) by gravity filtration and dried for 2 days in a 70° C. forced air oven.

Sulfonation of 2% Cross-linked poly(4-vinylbiphenyl) Gel

Dried poly(4-vinylbiphenyl) gel was transferred to a 40 mL glass vial. Concentrated sulfuric acid (10 mL) was added and the mixture was heated at 100° C. for 1 h. The resulting brown, swollen gel was allowed to cool to room temperature and was washed exhaustively with methanol by gravity filtration until the pH was 4-5. The gel was washed several times with water and then dried for 2 days in a 70° C. forced air oven.

Example 11

Preparation of poly(styrenesulfonate-co-styrene-n-N-octylsulfonamide)

Sodium poly(styrenesulfonate) (114.9 mmoles, 20 g) was dispersed in N,N-dimethylformamide ("DMF",100 mL, anhydrous). Thionyl chloride (114.9 mmoles, 9.95 mL) was added and the mixture was heated at 60° C. for 16 h. The mixture was poured over ice and neutralized with 50% NaOH (aq) until the pH was about 6.5. The solution was dialyzed through SpectraPor 6–8K MWCO dialysis tubing in 4×3 gallons of deionized water until the conductivity of the dialysate was 0.00 mS/cm. The sample was lyophilized to yield a white powder.

Poly(styrenesulfonate) w/10 mole % n-octylsulfanamide

Sodium poly(styrenesulfonate) (114.9 mmoles, 20 g) was dispersed in DMF (100 mL, anhydrous). Thionyl chloride (114.9 mmoles, 9.95 mL) was added and the mixture was heated at 60° C. for 16 h. n-Octylamine (11.486 mmoles, 1.8980 mL) was added and the mixture was stirred at for 5.5 h. The mixture was poured over ice and neutralized with 50% NaOH (aq) until the pH was 6.1. The solution was dialyzed through SpectraPor 6–8K MWCO dialysis tubing in 4×3 gallons of DI water until the conductivity of the dialysate was 0.00 mS/cm. The sample was lyophilized to yield a white powder.

Poly(styrenesulfonate) wl 20mole % n-octylsulfanamide

Poly(styrenesulfonate, Na) (114.9 mmoles, 20 g) was dispersed in DMF (100 mL, anhydrous). Thionyl chloride (114.9 mmoles, 9.95 mL) was added and the mixture was heated at 60° C. for 16 h. n-Octylamine (22.97 mmoles, 3.7967 mL) was added and the mixture was stirred at rt for 5.5 h. The mixture was poured over ice and neutralized with 50% NaOH (aq) until the pH was 6.7. The solution was dialyzed through SpectraPor 6–8K MWCO dialysis tubing in 4×3 gallons of DI water until the conductivity of the dialysate was 0.00 mS/cm. The sample was lyophilized to yield a white powder.

Poly(styrenesulfonate) w/ 30mole % n-octylsulfanamide

Poly(styrenesulfonate, Na) (114.9 mmoles, 20 g) was dispersed in DMF (100 mL, anhydrous). Thionyl chloride (114.9 mmoles, 9.95 mL) was added and the mixture was heated at 60° C. for 16 h. n-Octylamine (34.457 mmoles, 5.6950 mL) was added and the mixture was stirred at rt for 5.5 h. The mixture was poured over ice and neutralized with 50% NaOH (aq) until the pH was 6.5. The solution was dialyzed through SpectraPor 6–8K MWCO dialysis tubing in 4×3 gallons of deionized water until the conductivity of the dialysate was 0.00 mS/cm. The sample was lyophilized to yield a white powder.

Poly(styrenesulfonate) w/ 40mole % n-octylsulfonamide

Sodium poly(styrenesulfonate) (114.9 mmoles, 20 g) was dispersed in DMF (100 mL, anhydrous). Thionyl chloride (114.9 mmoles, 9.95 mL) was added and the mixture was heated at 60° C. for 16 h. n-Octylamine (55.131 mmoles, 7.5934 mL) was added and the mixture was stirred at room temperature for 5.5 h. The mixture was poured over ice and neutralized with 50% NaOH (aq) until the pH was about 6.7. The solution was dialyzed through SpectraPor 6–8K MWCO dialysis tubing in 4×3 gallons of deionized water until the conductivity of the dialysate was 0.00 mS/cm. The sample was lyophilized to yield a white powder.

Example 12

Synthesis of poly(styrenesulfonate) Calcium Salt

To a 500 mL 3-necked round bottomed flask were added 2 g of poly(sodium 4-styrene sulfonate) and 100 mL of deionized water. The mixture was stirred for several minutes until a homogeneous solution was obtained. To this polymer solution was added 6.46 mL of a 0.225 M solution of $CaCl_2$. The reaction mixture was allowed to stir at room temperature for 15 hr.

The reaction mixture was purified by membrane centrifugation using molecular weight 3K cut-off filters. The solution was dried at 70° C. in a forced air oven for 24 hours, yielding 1.4 g of the polymer as an off white solid.

Example 13

Preparation of Cross-linked Styrenesulfonate Copolymers with Hydrophobic Co-monomers Polystyrenesulfonate/hydrophobe gels were prepared by copolymerizing styrene sulfonate with acrylamide, n-butylacrylamide, n-decylacrylamide, or styrene with either divinylbenzene (2%) or N,N'-methylenebisacrylamide (8%) as the crosslinker as follows:

Polystyrenesulfonate Gel (2% Cross-linked)

Polystyrenesulfonate (29.4 mmoles, 5.119 g) and divinylbenzene (0.6 mmoles, 85.5 microL) were dissolved in 10 mL ethanol and 10 mL water in a 40 mL vial fitted with a septum cap. The solution was degassed by bubbling nitrogen through and 1 mole % AIBN was added as a solution. The polymerization solution was further degassed and the placed in a heated reaction block at 60° C. for 18 h. A clear, colorless gel formed.

Polystyrenesulfonate-co-acrylamide gel (75 mole %:23 mole %:2% Cross-linked)

Polystyrenesulfonate (22.5 mmoles, 3.918 g), acrylamide (6.90 mmoles, 0.490 g), and divinylbenzene (0.6 mmoles, 85.5 microL) were dissolved in 10 mL ethanol and 10 mL water in a 40 mL vial fitted with a septa cap. The solution was degassed by bubbling nitrogen through and 1 mole % AIBN was added as a solution. The polymerization solution was further degassed and the placed in a heated reaction block at 60° C. for 18 h. A clear, colorless gel formed.

Polystyrenesulfonate-co-n-butylacrylamide Gel (75 mole %:23 mole %:2% Cross-linked)

Polystyrenesulfonate (22.5 mmoles, 3.918 g), n-butylacrylamide (6.90 mmoles, 0.878 g), and divinylbenzene (0.6 mmoles, 85.5 microL) were dissolved in 15 mL ethanol and 5 mL water in a 40 mL vial fitted with a septa cap. The solution was degassed by bubbling nitrogen through and 1 mole % AIBN was added as a solution. The polymerization solution was further degassed and the placed in a heated reaction block at 60° C. for 18 h. A clear, colorless gel formed.

Polystyrenesulfonate/acrylamide/n-butylacrylamide Gel (75 mole %:11.5 mole %: 11.5 mole %: 2% Cross-linked)

Polystyrenesulfonate (22.5 mmoles, 3.918 g), acrylamide (3.45 mmoles, 0.245 g), n-butylacrylamide (3.45 mmoles, 0.439 g) and divinylbenzene (0.6 mmoles, 85.5 microL) were dissolved in 15 mL ethanol and 5 mL water in a 40 mL vial fitted with a septa cap. The solution was degassed by bubbling nitrogen through and 1 mole % AIBN was added as a solution. The polymerization solution was further degassed and the placed in a heated reaction block at 60° C. for 18 h. A clear, light yellow gel formed.

Polystyrenesulfonate-co-n-decylacrylamide Gel (75 mole %:23 mole % :2% Cross-linked)

Polystyrenesulfonate (22.5 mmoles, 3.918 g), n-decylacrylamide (6.90 mmoles, 1.458 g), and divinylbenzene (0.6 mmoles, 85.5 microL) were dissolved in 15 mL ethanol and 5 mL water in a 40 mL vial fitted with a septa cap. The solution was degassed by bubbling nitrogen through and 1 mole % AIBN was added as a solution. The polymerization solution was further degassed and the placed in a heated reaction block at 60° C. for 18 h. A creamy yellow gel formed.

Polystyrenesulfonate/acrylamide/n-decylacrylamide gel (75 mole %: 11.5 mole %: 11.5 mole %:2% cross-linked)

Polystyrenesulfonate (22.5 mmoles, 3.918 g), acrylamide (3.45 mmoles, 0.245 g), n-decylacrylamide (3.45 mmoles, 0.729 g) and divinylbenzene (0.6 mmoles, 85.5 microL) were dissolved in 15 mL ethanol and 5 mL water in a 40 mL vial fitted with a septa cap. The solution was degassed by bubbling nitrogen through and 1 mole % AIBN was added as a solution. The polymerization solution was further degassed and the placed in a heated reaction block at 60° C. for 18 h. A creamy yellow gel formed.

Polystyrenesulfonate-co-styrene gel (75 mole %:23 mole %:2% cross-linked)

Polystyrenesulfonate (22.5 mmoles, 3.918 g), styrene (6.90 mmoles, 0.7906 mL), and divinylbenzene (0.6 mmoles, 85.5 microL) were dissolved in 10 mL ethanol and 10 mL water in a 40 mL vial fitted with a septum cap. The solution was degassed by bubbling nitrogen through and 1 mole % AIBN was added as a solution. The polymerization solution was further degassed and the placed in a heated reaction block at 60° C. for 18 h. A clear, colorless gel formed.

Polystyrenesulfonatelacrylamide/styrene gel (75 mole %: 11.5 mole %: 11.5%; 2% cross-linked)

Polystyrenesulfonate (22.5 mmoles, 3.918 g), acrylamide (3.45 mmoles, 0.245 g), styrene (3.45 mmoles, 0.3953 mL) and divinylbenzene (0.6 mmoles, 85.5 microL) were dissolved in 10 mL ethanol and 10 mL water in a 40 mL vial fitted with a septum cap. The solution was degassed by bubbling nitrogen through and 1 mole % AIBN was added as a solution. The polymerization solution was further degassed and the placed in a heated reaction block at 60° C. for 18 h. A clear, colorless gel formed.

Polystyrenesulfonate-co-acrylamide Gel (50 mole %:48 mole %:2% Cross-linked)

Polystyrenesulfonate (15.0 mmoles, 2.612 g), acrylamide (14.4 mmoles, 1.024 g), and divinylbenzene (0.6 mmoles, 85.5 microL ) were dissolved in 5 mL ethanol and 15 mL water in a 40 mL vial fitted with a septa cap. The solution was degassed by bubbling nitrogen through and 1 mole % AIBN was added as a solution. The polymerization solution was further degassed and the placed in a heated reaction block at 60° C. for 18 h. A clear, colorless gel formed.

Polystyrenesulfonate/acrylamide/n-butylacrylamide Gel (50 mole %:24 mole %: 24 mole %:2% Cross-linked)

Polystyrenesulfonate (15.0 mmoles, 2.612 g), acrylamide (7.2 mmoles, 0.512 g), n-butylacrylamide (7.2 mmoles, 0.916 g) and divinylbenzene (0.6 mmoles, 85.5 microL) were dissolved in 5 mL ethanol and 15 mL water in a 40 mL vial fitted with a septum cap. The solution was degassed by bubbling nitrogen through and 1 mole % AIBN was added as a solution. The polymerization solution was further degassed and the placed in a heated reaction block at 60° C. for 18 h. A clear, colorless gel formed.

Polystyrenesulfonate/acrylamide/styrene Gel (50 mole %:24 mole %: 24 mole %:2% Cross-linked)

Polystyrenesulfonate (15.0 mmoles, 2.612 g), acrylamide (7.2 mmoles, 0.512 g), styrene (7.2 mmoles, 0.8250 mL) and divinylbenzene (0.6 mmoles, 85.5 microL) were dissolved in 10 mL ethanol and 10 mL water in a 40 mL vial fitted with a septa cap. The solution was degassed by bubbling nitrogen through and 1 mole % AIBN was added as a solution. The polymerization solution was further degassed and the placed in a heated reaction block at 60° C. for 18 h. A clear, colorless gel formed.

Polystyrenesulfonate-co-acrylamide gel (25 mole %:73 mole %:2% cross-linked)

Polystyrenesulfonate (7.5 mmoles, 1.306 g), acrylamide (21.9 mmoles, 1.557 g), and divinylbenzene (0.6 mmoles, 85.5 microL ) were dissolved in 5 mL ethanol and 15 mL water in a 40 mL vial fitted with a septa cap. The solution was degassed by bubbling nitrogen through and 1 mole % AIBN was added as a solution. The polymerization solution was further degassed and the placed in a heated reaction block at 60° C. for 18 h. A clear, colorless gel formed.

All samples were purified by splitting the gel into 2 portions in two 50 mL centrifuge tubes. The gels were washed a minimum of three times with ethanol or until the supernatant was clear and colorless. The total volume of ethanol used was roughly between 75 mL and 100 mL depending on the swelling index of the gel. The gels were dried in a forced-air oven at 60° C. for 2 days.

Gels were ground in a coffee grinder and sieved through 140, 230 mesh sieves. A 0.5–1 g sample of the 140–230 size gel particles was washed in 50 mL centrifuge tubes 3 times with water. Some samples were highly absorbent and had to be split up over multiple tubes. Generally, material in each tube was washed with a total of 20–80 mL of water. Samples were then washed 1× with MeOH, centrifuged, decanted, and dried for two days at 70° C. Gel was washed with a total of 20–80 mL of water.

Example 14

Preparation of poly(4-vinylbiphenylsulfonate)

Polymerization of 4-vinylbiphenyl

4-Vinylbiphenyl (166.4 mmoles, 30 g) was added to a 500 mL, 3-neck, round-bottom flask equipped with a reflux condenser, a J-Kem thermocouple, and a septun. Toluene (60 mL) was added and the solution was degassed for 1 h. AIBN (1 mole %, 0.294 mmoles, 0.2733 g) was added and the solution was degassed for a further 15 min. The polymerization mixture was heated at 60° C. for 21 h. The resulting clear brown solution was poured into 2 L of methanol and stirred for several hours. The fine brown powder was filtered and washed 3×500 mL methanol and dried overnight in a forced-air oven at 70° C. A fine brown powder was obtained (28.02 g, 93.40% yield).

Sulfonation of Poly(4-vinylbiphenyl)

Poly(4-vinylbiphenyl) was mixed with concentrated sulfuric acid (100 mL) and heated at 100° C. for 8 h. The mixture eventually turned to a clear brown viscous solution. The polymer solution was poured into ice and neutralized to pH 6.2 with 50% aqueous NaOH. The solution was dialyzed through dialysis membrane have a molecular weight cut-off of 3.5 K in 4 times 5 L deionized water. The conductivity of the dialysate was <0.1 mS/cm. The water was removed by distillation on a rotary evaporator to yield a clear brown flaky solid.

Example 15

Preparation of Poly(2-vinylnaphthalenesulfonate)

Polymerization of 2-vinylnaphthalene

2-Vinylnaphthalene (194.5 mmoles, 30 g) was added to a 500 mL, 3-neck, round-bottom flask equipped with a reflux condenser, a J-Kem thermocouple, and a septum. Toluene (60 mL) was added and the solution was degassed for 1 h. AIBN (1 mole %, 0.294 mmoles, 0.3195 g) was added and the solution was degassed for a further 15 min. The polymerization mixture was heated at 60° C. for 21 h. The resulting clear brown solution was poured into 2 L of methanol and stirred for several hours. The fine brown powder was filtered and washed 3×500 mL methanol and dried overnight in a forced-air oven at 70° C. A fine brown powder was obtained (28.45 g, 94.83% yield)

Sulfonation of poly(2-vinylnaphthalene)

Poly(2-vinylnaphthalene) was mixed with concentrated sulfuric acid (100 mL) and heated at 100° C. for 8 h. The mixture eventually turned to a clear brown viscous solution. The polymer solution was poured into ice and neutralized to pH 6.4 with 50% aqueous NaOH. The solution was dialyzed through dialysis membrane have a molecular weight cut-off of 3.5 K in 4 times 5 L deionized water. The conductivity of the dialysate was <0.1 mS/cm. The water was removed by distillation on a rotary evaporator to yield a clear brown flaky solid.

Example 16

Poly(sodium 4-styrene sulfonate-co-(-)-menthyl-4-styrene sulfonate), 5 % (−)- menthol To a mixture of poly(sodium 4-styrene sulfonate) (30.0 g; 0.145 mol of sulfonate) in 300 mL of anhydrous DMF stirred at room temperature thionyl chloride (17.3 g; 0.145 mol) was added. The addition was done slowly insuring that the temperature did not go above 50° C. Stirring was continued overnight and then one third of the reaction mixture was treated with pyridine (0.764 g; 00966 mol). After stirring at room temperature for 2.5 h, (−)-menthol (0.375 g; 0.00240 mol) was added and the resulting reaction mixture was stirred at room temperature overnight and then at 50° C. for 3 h. The mixture was then poured slowly into one liter of water containing sodium bicarbonate (5 g). After the addition was complete more sodium bicarbonate was added until the bubbling stopped and the pH was neutral. Exhaustive dialysis followed by drying with a flow of air gave a white solid.

Example 17

Synthesis of Poly(sodium 4-styrene Sulfonate-co-Lithocholyl Acid -4-styrene Sulfonate), 5 % Lithocholic Acid To a mixture of poly(sodium 4-styrene sulfonate) (30.0 g; 0.145 mol of sulfonate) in 300 mL of anhydrous DMF stirred at room temperature thionyl chloride (17.3 g; 0.145 mol) was added. The addition was done slowly insuring that the temperature did not go above 50° C. Stirring was continued overnight and then one third of the reaction mixture was treated with pyridine (0.764 g; 00966 mol). After stirring at room temperature for 2.5 h, lithocholic acid (0.904 g; 0.00240 mol) was added and the resulting reaction mixture was stirred at room temperature overnight and then at 50° C. for 3 h. The mixture was then poured slowly into one liter of water containing sodium bicarbonate (5 g). After the addition was complete more sodium bicarbonate was added until the bubbling stopped and the pH was neutral. Exhaustive dialysis followed by drying with a flow of air gave a white solid.

The in vivo hamster assay was also used as described above to assess the efficacy of the following polymers, as shown in Table 1.

Example 18

Poly(sodium 3-styrene sulfonate) with 40% Metronidazole

Poly(sodium 4-styrene sulfonate (160-246-001, 25 g) was dissolved in deionized water (500 ml) in a 3 liter plastic bucket using a magnetic stir plate. Into a separate, appropriately sized beaker, metronidazole (8.32g) was dissolved in deionized water (600 ml) and 1 M HCl (0.75 eq). This metronidazole solution was slowly poured into the poly (sodium 4-styrene sulfonate) solution. The resulting solution was stirred at room temperature for approximately 17 hours. It was placed in dialysis bags (6–8K MWCO) until a conductivity of <0.05 was obtained. The polymer solution was dried in a forced air oven at 70° C. Approximately 22 g of the polymer was obtained. Analysis by HPLC showed a 13.8% loading of metronidazole.

Example 19

Sulfonation of Poly(4-methoxystyrene)

Poly(4-methoxystyrene) (1g) was placed in a 30 ml vial. Concentrated sulfuric acid (5 ml) was added to the vial. While stirring, this was heated at 100° C. for 8 hours. After the 8 hours, the polymer was dissolved (clear, dark solution). Deionized water was added (50 ml). the sample was neutralized by adding NaOH (50% soln.) drop-wise. It was placed in dialysis bags (6–8K MWCO) until a conductivity of <0.1 was reached. The polymer solution was filtered and then dried on the speed vac.

Example 20

Sulfonation of Poly(diphenoxyphosphazene)

Poly(diphenoxyphosphazene) (1 g) was placed in a 30 ml vial. Concentrated sulfuric acid (5 ml) was added to the vial. While stirring, this was heated at 100° C. for 8 hours. After the 8 hours, the polymer was dissolved (clear, yellow solution). Deionized water was added (50 ml). the sample was neutralized by adding NaOH (50% soln.) drop-wise. It was placed in dialysis bags (6–8K MWCO) until a conductivity of <0.1 was reached. The polymer solution was filtered and then dried on the speed vac.

Example 21

Sulfonation of Ethylene Oxide-Styrene-Ethylene Oxide Block Copolymer

Ethylene oxide-styrene-ethylene oxide block copolymer (900 mg) was placed in a 30 ml vial. Concentrated sulfuric acid (5 ml) was added to the vial. While stirring, this was heated at 100° C. for 8 hours. After the 8 hours, the polymer was not dissolved. More concentrated sulfuric acid (5 ml) was added to the vial. It was then heated at 110° C., with stirring, for another 8 hours. This was repeated two more times. A total of 20 ml of concentrated sulfuric acid was added (5 ml, 100° C., 8 hours; 15 ml, 110° C., 24 hours). Deionized water was added (50 ml). The sample was neutralized by adding NaOH (50% soln.) drop-wise. It was placed in dialysis bags (6–8K MWCO) until a conductivity of <0.1 was reached. The polymer was filtered (a lot of insoluble material remained) and then dried on the speed vac.

Example 22

Co-administration of poly(styrenesulfonate) and poly(diallylmethylamine)

Soluble polystyrene sulfonate and cross-linked $C_8$-alkylated polydiallylmethylamine (PDMA) are both able to reduce mortality from *C. difficile* infection in the hamster model of *C. difficile* colitis. These polymers exhibit different toxin binding properties in vitro. Polystyrene sulfonate binds *C. difficile* Toxin A and protects cells in culture from Toxin A mediated cell rounding. Cross-linked $C_8$ alkylated PDMA binds Toxins A and B in vitro and can protect cells in culture from toxin mediated cell rounding. This polymer is about five times more potent for binding Toxin B than binding Toxin A in vitro. To gain the benefit of optimal Toxin A and B binding, these polymers were tested in combination in the hamster model of *C. difficile* colitis. Treatment with polymer began 24 hours prior to infection with *C. difficile*. Hamsters were give 3 daily doses of polymer at 8 am, 12 pm, and 4 pm each day. Hamsters were treated for a total of 7 days with saline (control), polystyrene sulfonate alone, cross-linked, $C_8$ alkylated PDMA alone, or a combination of the two polymers administered in separate doses (2 doses of polystyrene sulfonate, 1 dose of $C_8$ PDMA). Animals were observed for a total of 7 days. None of the saline treated animals survived treatment. The polystyrene sulfonate treated animals had a 80% survival on day 7, with the survivors showing mild or moderate disease. The $C_8$ alkylated PDMA animals had a 50% survival on day 7, with the survivors showing moderate or no disease. The combination of the polystyrene sulfonate and the $C_8$ alkylated PDMA resulted in a 90% survival on day 7, with 80% of the animals showing no disease. Therefore, combination of soluble polystyrene sulfonate and $C_8$ alkylated PDMA appears to be an effective therapy for *C. difficile* colitis in vivo.

Example 23

Toxin Binding Assays

ELISA

An enzyme linked immunosorbant assay (ELISA) is available commercially for diagnosis of *C. difficile* toxin levels in stool samples. This assay uses microtiter plates coated with purified monoclonal antibodies to *C. difficile* toxins A and B to bind toxin in solution. The bound toxins are then detected with an affinity purified polyclonal antisera that has been linked with the enzyme horseradish peroxidase ("HRP"). Unbound antibody is washed away and the antibody-bound toxin is then detected with a colored substrate for the HRP. The assay is sensitive to nanogram quantities of Toxins A and B. This ELISA assay was used to determine free toxin levels after incubation of purified Toxin A or B with a variety of polymers in the presence of hamster cecal contents, which were used to provide physiologically relevant conditions predictive of in vivo toxin binding.

To perform the ELISA assay, polymer (10 mg) was weighed out into each of four 1.5 ml Eppendorf tubes. 500 µL cecal contents were then added to each tube, and the tubes were then mixed on a Vortex and placed on the nutator for 1 hour. 500 µL of a 200 ng/mL or 2000 ng/mL solution of Toxin A or Toxin B in phosphate buffer was then added to each tube to produce a final toxin concentration of 1000 ng/mL or 100 ng/mL. The tubes were then vortexed again and then placed on the nutator for another hour. The tubes were then centrifuged.

100 µl of diluted supernatant from each tube was added to each well of a plate, avoiding solid material. 100 µl of conjugate 1 was added to each well. The wells were covered with a plate sealer and incubated at 37° C. for 1 hour. The wells were aspirated into a biohazard receptacle (reservoir containing wescodyne or 10% bleach in water). The plate was washed using a plate washer, filling the wells with 300 µL of wash buffer. After the final wash the plate was inverted and banged to remove any residual wash buffer on paper towels. 100 µl of diluted step 2 conjugate was added to each well. The plate was covered and incubated 20 min. at room temperature. The wells were washed five times using the plate washer, as above, and then banged to remove residual buffer. 100 µl of substrate mix was added to each well, then the plate was sealed and incubated 15 min. at room temperature. 150 µL of stop solution was then added to each well, and the plate was mixed gently by swirling plate on bench. The absorbance at 450 nm was read immediately.

Cell Culture Assay

*C. difficile* toxins cause rounding of cells in culture. This property can be used to screen for inhibition of toxin activity by polymeric compounds. Sensitivities to toxins A and B differ among different cell lines. In the present case, Vero cells (ATCC cell line) were used. These cells are sensitive to 600 pg of Toxin A and less than 2 pg of Toxin B. The assay was run by plating Vero cells in 12 well transwell plates or 96 well microtiter plates. The cells were seeded 24 hours prior to testing, and were confluent monolayers at the time of toxin addition. Polymers (5 mg/ml) were incubated in tissue culture media (Minimal Essential Media with 10% fetal bovine serum) with Toxin A or Toxin B for 1 hour at room temperature with rocking. Following incubation, samples were handled differently, depending on whether they were insoluble gels or soluble polymers. Insoluble gels were added to transwells (0.5 ml/well), since direct addition of the gels to the monolayer would obscure the cells, preventing detection of cell rounding. Soluble polymers were added directly to cell monolayers in 96 well microtiter plates (0.1 ml/well). Cells were incubated at 37° C. for 18 hours and observed for cell rounding. The endpoint of the assay was scored as the lowest concentration of polymer that can protect 50% and 100% of the monolayer from cell rounding at 18 hours incubation. Controls included an active polymer incubated with toxins A and B, toxins A and B alone, and each polymer alone without toxin.

Rat Ileal Loop Model Assay

The objective of this assay was to measure the ability of polymeric compounds to prevent Toxin A mediated fluid accumulation and permeability in a ligated section of rat ileum. Rats were anesthetized and a 5 cm section of rat ileum was ligated with silk suture. Polymer (1–5 mg) and 5 µg of purified Toxin A were injected into this section. The rat also received an intravenous injection 10 µCi of $^3$H mannitol as a marker for intestinal permeability. Toxin A increases vascular permeability in the intestine, allowing the mannitol to enter the loop. Four hours after injection of Toxin A and polymer, the ileal loop sections were removed, weighed and total fluid accumulation was measured. Accumulation of $^3$H mannitol was measured by liquid scintillation counting. Polymeric compounds that bind Toxin A will block the intestinal fluid accumulation and permeability to $^3$H mannitol. The endpoint of the assay is the concentration of polymer that completely inhibits Toxin A mediated fluid accumulation and permeability. A modification of this assay involved administration of the polymer by oral gavage. Rats received 250 mg/kg in solution by oral gavage 90 minutes prior to preparation of ileal loops. Toxin was injected into ileal loops as described above.

Results

Results of the ELISA, cell culture, rat ileal loop and hamster assays are presented in Table 1 for a variety of polymers. Also included are corresponding data for cholestyramine, a cationic polymer which has been used clinically to neutralize *C. difficile* toxins.

TABLE 1

| | Results of biological assays | | | |
|---|---|---|---|---|
| | Toxin Binding (in vitro) concentration of toxin neutralized by 5 mg/ml | Rat Loop Dose Inhibiting 5 µToxin A | | Hamster % survival on |
| Polymer | polymer solution | (direct) | (gavage) | day 5 |
| Sodium polystyrene sulfonate | A = 10 ng/ml<br>B = 0.004–0.008 ng/ml | 2–5 mg | 250 mg/kg | 90% |
| Polystyrene sulfonate, 15% Ca++ | A = 10 ng/ml<br>B = ND | <0.5 mg | ND | 80% |
| Polystyrene sulfonate 5% menthol | A = 10 ng/ml<br>B = 0.004 ng/ml | 2.5 mg | ND | 90% |
| Cholestyramine | A = <0.015 ng/ml<br>B = <0.015 ng/ml | >20 mg | ND | 10% |

The data presented for the hamster model indicate per cent survival at day 5 following inoculation with *C. difficile*.

The results presented in Table 1 indicate that each of the polystyrenesulfonate polymers tested is more effective in each of the assays than cholestyramine.

In Vivo Tests

Basic Protocol

Hamsters are highly sensitive to infection with *C. difficile* and develop a fatal colitis when disease is initiated by treatment with antibiotics. Compounds were evaluated for their ability to inhibit the activity of *C. difficile* toxins the hamster model of *C. difficile* colitis. Male hamsters (80–100 g) were purchased Biobreeders Inc. (Falmouth Mass.). All animals were maintained in groups of five in microisolator cages on autoclaved bedding (Beta Chips) and given free access to autoclaved chow and autoclaved, filtered water. Animals were rested approximately 1 week following arrival and prior to initiation of a study. A *C. difficile* strain initially isolated from a human *C. difficile* colitis was used to infect the animals. This strain (HUC2–4) produces moderate to high levels of toxins in vitro and in vivo. A suspension of $10^6$–$10^7$ bacterial cells/ml was prepared from an overnight broth culture and 0.1 ml was administered by oral gavage on day −1. Twenty-four hours later, each animal was injected subcutaneously with Cleocin Phosphate IV® at a dose of 10 mg/kg. Polymers were administered to groups of ten animals by gavage three times daily (t.i.d). The dose of polymers was 25–100 mg/day, administered in three divided doses of 0.75 ml each. Initiation and duration of dosing varied according to the treatment regimens as described below. Animals were observed daily for morbidity or mortality. Additional parameters assessed were general appearance, time to onset of clinical signs, and presence or absence of diarrhea ("wet tail"). Animals judged to be in extremis and surviving animals at the end of the study were painlessly euthanized by asphyxiation with 100% $CO_2$. Cecal contents were obtained in some studies and frozen for later toxin analysis.

Administration of clindamycin (on day 0) predictably induced disease in hamsters infected with *C. difficile* (on day −1) by eliminating the normal colonic flora and allowing *C. difficile* to proliferate. *C. difficile* leads to fatal colitis in 90–100% of infected hamsters within 2–4 days. The primary endpoint of the assay is the protection of the hamsters from mortality. This is a very severe and challenging model and CDAD in hamsters is much more aggressive disease, in both severity and time course, compared with the human form of the disease. Pharmaceutical compositions of the invention have been evaluated using the hamster model of CDAD using two different treatment paradigms. In the prophylaxis model, the studies have been designed to determine the potential for pretreatment with the toxin binders to prevent CDAD, despite the development of a toxingenic *C. difficile* infection. In the therapeutic model, the compositions are administered after the development of CDAD.

Prophylaxis Model

In this model four differrent doses (25, 50, 75 or 100 mg/day administered orally in three doses of 0.750 ml) of a pharmaceutical composition of polystyrene sulfonate (or saline control) was administered to male Syrian golden hamsters (ten animals per test group and ten animals per test group) orally for 7 days, from day −2 to day 5. hamsters were inoculated with *C. difficile* (Onderdonk strain (G69)) on day −1 and treated with clindamycin on day 0. In animals that received placebo control, 100% developed disease and were dead at day 3. In contrast, prophylaxis with the composition led to survival of 70% and 90% of the animals in the 50 mg/day dose and 100 mg/day dose groups, respectively. Although all of the animals experienced a toxin-producing *C. difficile* infection, the composition comprising polystyrene sulfonate effectively inhibits the toxins and minimizes the colitis during the period of altered colon flora. As the normal flora recover, *C. difficile* appears unable to compete and is reduced to a non-pathogenic level. Thus having a toxin binder on board during the initial stages of toxin exposure and preventing colitis before it developes.

Therapeutic Model

Polymer therapy was initiated on day 1 at a dose of 25, 50, 75 or 100 mg/day. Polymer was administered three times daily in 0.7–1.5 ml of sterile saline t.i.d. from day 1 through day 7 for a total of 7 days of treatment. Animals were observed for morbidity, mortality and clinical signs of disease for 7–14 days following the end of treatment.

Combination Therapy Model

Animals were administered a combination of 50–100 mg/day of polymer and antibiotic in a total volume of 0.75 ml saline from day 1 (48 hours after administration of pathogen) through day 5. The antibiotic was either metronidazole or vancomycin. The dose of metronidazole was 21 mg/day. The dose of vancomycin was 3 mg/day. Following combination therapy, animals were dosed for an additional 4 days with 50–100 mg/day of polymer alone. Animals were observed for morbidity, mortality and clinical signs of disease for 7–14 days following the end of treatment.

Metronidazole is effective in preventing death from CDAD in hamsters as long as the drug is being actively administered. However, at the conclusion of therapy, 80–90% of animals have a relapse/recurrence of CDAD and die within 3–6 days of discontinuing metronidazole. Experiments show the effectiveness of a polystyrene sulfonate (PSS) composition admininstered as treatment after CDAD onset and in the prevention of relapse. Mortality from *C. difficile* relapse after withdrawal of metronidazole was prevented in 90% of the animals treated with a high dose of a composition comprising polystyrenesulfonate. Relapse was prevented in 70% of animals in the low dose polystyrene sulfonate group. None of the saline treated controls survived. Only 20% of the animals treated with metronidazole alone survived 16 days after the last dose of antibiotic (surviving animals contained to have diarrhea at day 21). Thus, inhibition of the toxins by the PSS composition prevented colitis and other associated pathology during the time necessary for the normal flora to recover after metronidazole therapy appears to prevent the development of relapse.

Monotherapy with PSS Compositions

Treatment with PSS composition alone was also studied and compared with the current standard of care, metronidazole alone. The PSS compostion in accordance with the invention was superior to metronidazole, preventing 40% of animals compared with 20% in the metronidazole alone group. This result in a rigorous model suggests that the PSS composition is superior to metronidazole as monotherapy. PSS compositions did not appear to interfere with the activity of antibiotics.

Procedure for Vero Cell Culture Assay

For all screens Vero cells were used in the 96 well format with $4 \times 10^4$ cells per well, with 100 μl per well. The plates were incubated overnight at 37° C. to be utilized the following day. All media, plates, pipettes and equipment used for the culture was kept sterile. Plates were covered and sprayed with EtOH before being placed in the incubator.

Regular Toxin A and B Screen

Polymers were weighed out in 15 ml. conical tubes with 10 mg/ml to start, with the final concentration in the wells at 5 mg/ml. Usually the tubes had about 40 mg to 4 ml of media, as diluent. The excess was kept in the 4° C. refrigerator in case a re-test needs was desired. The media was pipetted into the tubes sterilely and the tubes were then vortexed thoroughly. If the polymer was not in solution, the tubes were placed in a 37° C. water bath for 15–20 minutes. For this experiment the Toxin A concentrations were 10 ng/ml and the Toxin B was 1 ng/ml final. The Toxins and polymer were made up 2× and mixed 1:1 to give a final concentration of 1× for both. These solutions were made in conical tubes and placed on ice.

Once the polymers were thoroughly dissolved, sterile 96-well plates were gathered and media placed at 100 μl per well in rows G-H as well as columns 2–6 and 8–12 in rows A–F. Four polymers were screened per plate and each polymer had three rows, one for polymer and media alone, one for Toxin A and polymer and one for Toxin B and polymer. The set-up is as follows:

| | |
|---|---|
| Polymer 1: | Polymer alone - Row A, col. 1–6 |
| | Polymer + A -- Row B, col. 1–6 |
| | Polymer + B -- Row C, col. 1–6 |
| Polymer 2: | Polymer alone - Row D, col. 1–6 |
| | Polymer + A -- Row E, col. 1–6 |
| | Polymer + B -- Row F, col. 1–6 |
| Polymer 3: | Polymer alone - Row A, col. 7–12 |
| | Polymer + B -- Row C, col. 7–12 |
| | Polymer + A -- Row B, col. 7–12 |
| Polymer 4: | Polymer alone - Row D, col. 7–12 |
| | Polymer + A -- Row E, col. 7–12 |
| | Polymer + B -- Row F, col. 7–12 |

After the media was added, 200 µl of the polymer solution was added to the first columns in each segment (col. 1 or 7) and diluted two-fold across the plate to the end of the section (col. 6 or 12). Media was added to rows A, D, and H and Toxin A was added to rows B, E, and G (col. 1–6). Toxin B was added to rows C, F and G (col. 7–12). Toxin and media were both added at 100 µl per well, bringing the total volume in the well up to 200 µl. The last row (H) was not used in the assay. The plates were then placed on a shaker and incubated at room temperature for one hour.

Plates with cells that had been kept overnight in the incubator were then taken out and the media from the wells was pipetted off using a vacuum suction apparatus. Media is removed from only one plate at a time, as the cells tended to dry out during the process. After removal of media, the toxin/polymer mixture was pipetted onto the cells. Solution was added at 100 µl per well from the least amount of toxin to the most concentrated wells, using the same pipette tips throughout the procedure. The pipette tips were changed for each new polymer run. Row H was left untouched and the plates were then examined under the microscope to insure that the monolayer of cells was not damaged during suction. The plates were then put back into the 37° C. incubator and checked at 18 hours post polymer/toxin treatment and scored for cell rounding, no cell rounding or partial (50%) cell rounding.

Toxin B Dose-Down

Polymers were weighed at 10 mg/ml (5 mg/ml final) in conical tubes. Usually about 70 mg to 7 ml media (the diluent used) was adequate to complete a run. They were vortexed into solution. Polymers that were not in solution were placed in the 37° C. water bath for 15–20 minutes. Solutions that were still unable to dissolve completely were noted and gels were run with the gel procedure. Toxin B was made starting at 2 ng/ml (1 ng/ml final) and kept on ice. Sterile 96-well plates were used and media was added at 100 µl per well to all wells except the first column. Each polymer was tested on three different rows (two polymers per plate), the first row for polymer alone with no toxin and the next two with polymer and Toxin B. Row G was a dose-down of Toxin B alone and row H was left untreated. The set-up was as follows:

| | |
|---|---|
| Polymer 1: | Row A (1–12) - Polymer alone |
| | Row B (1–12) - Polymer with Toxin B |
| | Row C (1–12) - Polymer with Toxin B |
| Polymer 2: | Row D (1–12) - Polymer alone |
| | Row E (1–12) -- Polymer with Toxin B |
| | Row F (1–12) -- Polymer with Toxin B |
| Extra rows: | Row (1–12) -- Dose down of Toxin B alone |
| | Row H -- Untreated |

200 µl of either media or Toxin B were placed in the first column (media for rows with polymer alone) and this was diluted two-fold across the plate, carrying over 100 µl to each new column. Polymer mixture was added at 100 µl to all well except for row G and H. Row substituted 100 µl of media and row H was left blank. These plates were put on a shaker for one hour and the procedure from above was followed from this step on.

When toxin and polymer had been added to the cells, the plates were then sprayed with EtOH, placed in the 37° C. incubator overnight, and scored 18 hours later. Scoring was positive for cell rounding, negative for normal cells and +/–for wells with the morphology at least 50% normal.

Procedure for Gels

Gels were run at two different concentrations of polymers with concentrations of either 5 or 10 mg/ml. Concentrations of toxins were at 100, 10, 1 for Toxin A and B. These concentrations varied, depending on polymer type. Twelve Eppendorf tubes were weighed for each polymer. Toxins were made at the 1x dilution and 1 ml. of toxin added to the appropriate Eppendorf tube. Control tubes were used with polymer alone (at all concentrations) and with toxins alone. The tubes were then nutated at room temperature for one hour and centrifuged for five minutes at 14,000 rpm. 200 µl of each sample was placed in a well on sterile 96-well plates. Plates with Vero cells were removed from the incubator and the media removed via suction (one plate at a time). 100 µl of the toxin/polymer mixture was added directly to the plates with cells and the plates were covered and placed into the incubator overnight for scoring the next day. Scoring employed the procedures above.

Rat Ileal Loop Experiments

This protocol describes the preparation of ileal loops in anesthetized rats. This experimental model can be used to test the effects of enterotoxic agents such as bacterial toxins on intestinal structure and function; the effects of putative protective agents can also be determined.

Two intestinal loops about 5 cm in length were prepared in each animal by ligating the ileum with silk suture. The renal pedicles were ligated to prevent the excretion of mannitol, and radiolabelled mannitol ($^3$H-mannitol) injected i.v. Test agents (±toxin ±polymer) were then injected into these loops. Four hours later the animals were sacrificed and the loops harvested. Intestinal fluid secretion (an index of secretory diarrhea) was estimated by weighing the loops and measuring their length. The permeability of the intestinal mucosa was estimated by measuring the accumulation of radiolabelled mannitol ($^3$H-mannitol) into the loop. Tissue samples were also placed in fixative for subsequent morphological evaluation of mucosal injury and inflammation.

Animal Preparation

Male Wistar rats 200–250 g were fasted overnight (18–22 hours) in wire bottom cages, to minimize copraphagy. Water was available ad libidum. The ileal loops were substantially free from luminal contents (food and bile) that could bind to or denature the toxin or the test agents used.

Solution Preparation

Each ileal loop received a 0.5 ml volume of a test agent or agents in PBS. Four sets of labelled tubes and labelled syringes were prepared (±toxin ±polymer). Toxin A adheres to plasticware, thus reducing its effective concentration. For this reason tubes and syringes should be reused between loops.

Toxin A

Toxin A was commercially prepared by TechLab Inc. and was provided in 0.5 ml vials containing 2 mg/ml. Each loop receiving Toxin A was administered 5 µg in total or 2.5 µl of the above solution.

Polymer

Loops receiving polymer received a total of 10 mg in a volume of 0.5 ml PBS (20 mg/ml). New polymer solutions/suspensions were prepared before each experiment.

$^3$H-Mannitol

A stock solution 1 mCi/ml $^3$H-mannitol (Mannitol, D-[1-$^3$H(N)]-, NEN Catalog No. NET101) was refrigerated. Each animal received 10 µCi of $^3$H-mannitol injected i.v. in a volume of 200 µl (ie. 10 µl stock $^3$H-mannitol +190 µl PBS per animal).

Anesthesia

Animals were anesthetized with 35–60 mg/kg pentobarbital i.p. (50 mg/ml solution.) Thus, an i.p. injection of 0.2–0.3 ml anesthetizes a 200–250g rat. As an alternative, a ketamineixylazine cocktail can be used. This cocktail can be prepared by mixing 5.4 ml of ketamine (100 mg/ml) and 0.45 ml of xylazine (100 mg/ml). Animals were anesthetized with 0.25–0.3 mls of this cocktail. Ten—fifteen minutes for anesthesia to be induced was allowed. Surgical stage anesthesia was confirmed by the lack of response from a painful stimulus (toe pinch).

Surgical Preparation

A midline abdominal incision was made and the cecum and small bowel exteriorized. A length of 3.0 silk was placed around the left renal pedicle and the vasculature ligated. The viscera was then positioned so as to expose the right kidney and the renal pedicle ligated, being careful not to damage the vena cava. The cecum was then positioned so as to visualize the small bowel and the vasculature supplying it. Two 5 cm lengths of ileum were identified that were free of luminal contents (foodstuff or bile) and ligatures tied so as to form two blind loops. The loops were then injected with the desired test agents. Agents were injected into the loop below the ligature distal to the cecum. The viscera was then positioned so as to visualize the vena cava and 200 µl of the $^3$H-mannitol solution injected i.v. Light pressure was applied to the puncture wound after withdrawing the needle to promote clotting. Following injection of mannitol viscera were placed back into the abdomen and the muscle and skin layers of the wound closed with surgical staples.

Injecting Ileal Loops

5 µg of Toxin A was dissolved in 0.5 ml of PBS (±polymer) and the mixture loaded into a syringe and injected into a loop. The contents of the syringe are then quickly injected into the intestinal loop.

Maintaining the Animals

Following surgery, animals were placed in a shoebox cage with wood chips and allowed to recover for a 4-hour period. Animals regained consciousness during this period. Any animals showing overt signs of pain or distress were euthanized immediately.

Harvesting and Processing the Loops

Four hours after test substances were administered, the ileal loops was harvested. Animals were sacrificed using 100% $CO_2$, the abdomen opened and the loops identified visually and by using the suture markers. Loops were trimmed of excess tissue and surgically excised, making sure not to lose any of the loop contents. The loops were laid on a piece of weighing paper, their length measured and the loop weight measured. The distal end of the loop was then placed in a pre-weighed vial and cut open so as to collect its contents. 500 µl of PBS was then injected into the proximal end of the loop to help wash the contents through. The loop was then cut in half and a 0.5 cm section isolated, opened and placed in fixative.

Sample Preparation for Scintillation Counting

Tubes were reweighed to determine the volume of the loop contents. The tubes were vortexed vigorously and 200 µl sample aliquoted to a 7 ml plastic scintillation vial. These samples were mixed with 5 mls of Ultima Gold scintillation cocktail and vortexed. Samples were allowed to equilibrate overnight (to minimize chemiluminescence), vortexed and counted the next day.

MIC Assay

The minimum inhibitory concentration (MIC) assay determines the minimum concentration of an antimicrobial agent required to inhibit growth of the test organisms. MIC assays were performed against a standard panel of organisms as a screening tool to identify compounds that have antimicrobial activity. The MIC assay was subsequently repeated against other specialized microbial panels; compounds were tested for biocidal activity, tested for time course of killing, tested for toxicity against tissue culture cells grown in vitro, and in some cases tested for antimicrobial activity in vivo.

The MIC assay was performed according to the Performance Standards for Antimicrobial Susceptibility Testing, 1998, vol. M100-S8, Eighth Informational Supplement, NCCLS, 940 West Valley Road, Suite 1400, Wayne, Pa. 19087.

Briefly, polymers to be tested were dissolved in 0.85% saline to a final concentration of up to 5000 µg/ml, the pH was adjusted to 7.0 and the solution was filter-sterilized through a 0.22 µm filter. Two-fold serial dilutions of polymer were prepared in Mueller-Hinton broth with cations aliquotted into 96-well microtiter plates. The plates were then inoculated with $5 \times 10^5$ cells/well of target organism, and incubated 18–24 hr at 35° C. The optical density (OD) was then read at 590 µm, and microorganism growth was scored (OD>0.1 is considered to be growth; OD<0.1 is considered growth inhibition). The MIC value was defined as the lowest concentration of compound which inhibits growth.

Organisms tested include a broad panel of aerobic gram negative and gram positive bacterial strains of clinical significance, a single anaerobe species (*Clostridium difficile*) as well as several strains of Candida spp.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of treating *C. difficile* associated diarrhea in a mammal comprising administering to said mammal a pharmaceutical composition comprising (poly)styrenesulfonate.

2. A method for treating antibiotic-associated diarrhea in a mammal comprising administering to said mammal a therapeutically effective amount of a composition comprising polystyrene sulfonate.

3. A method for treating *C. difficile* associated diarrhea in a mammal comprising administering to said mammal a therapeutically effective amount of a composition comprising polystyrene sulfonate.

4. A method of inhibiting the onset of antibiotic associated diarrhea in a susceptible mammal comprising administering to said mammal, a composition comprising polystyrene sulfonate in an amount sufficient to inhibit the onset of antibiotic associated diarrhea.

5. A treatment regimen for inhibiting the onset of antibiotic associated diarrhea in a susceptible mammal comprising administering simultaneously or sequentially, as a single treatment episode, a combination of a broad spectrum antibiotic and a therapeutically effective amount of a composition comprising polystyrene sulfonate.

6. A method of inhibiting relapse of antibiotic associated diarrhea in a susceptible mammal comprising administering to said mammal, a composition comprising polystyrene sulfonate in an amount sufficient to inhibit the relapse of antibiotic associated diarrhea.

7. A treatment regimen for inhibiting the relapse of antibiotic associated diarrhea in a susceptible mammal comprising administering simultaneously or sequentially, as a single treatment episode, a combination of a broad spectrum antibiotic and a therapeutically effective amount of a composition comprising polystyrene sulfonate.

8. The treatment regimen of claim 7 herein said antibiotic is metronidazole or vancomycin.

9. A treatment regimen for treating active *C. difficile* associated diarrhea in a mammal comprising administering simultaneously or sequentially, as a single treatment episode, a combination of an antibiotic effective against *C. difficile* and a therapeutically effective amount of a composition comprising polystyrene sulfonate.

10. The treatment regimen of claim 7 wherein said antibiotic is metronidazole or vancomycin.

11. The method of claim 2 wherein the polymer is soluble.

12. The method of claim 11 wherein the polymer has a molecular weight ranging from about 400,000 to 1 million Daltons.

13. The method of claim 12 wherein the polymer has a molecular weight of about 600,000 Daltons.

14. A pharmaceutical composition comprising polystyrene sulfonate and metronidazole or vancomycin.

15. The method of claims 4 therein the antibiotic associated diarrhea is *C. difficile* associated diarrhea.

16. The method of claim 5 wherein the antibiotic associated diarrhea is *C. difficile* associated diarrhea.

17. The method of claim 6 wherein the antibiotic associated diarrhea is *C. difficile* associated diarrhea.

18. The method of claim 7 wherein the antibiotic associated diarrhea is *C. difficile* associated diarrhea.

19. The pharmaceutical composition of claim 14 further comprising a pharmaceutically acceptable carrier or diluent.

* * * * *